(12) United States Patent
Moszner et al.

(10) Patent No.: US 11,142,592 B2
(45) Date of Patent: Oct. 12, 2021

(54) POLYMERIZABLE COMPOSITIONS WITH ACYLTIN PHOTOINITIATORS

(71) Applicants: Ivoclar Vivadent AG, Schaan (LI); Technische Universität Wien, Vienna (AT)

(72) Inventors: Norbert Moszner, Mauren (LI); Urs Karl Fischer, Arbon (CH); Peter Burtscher, Rankweil (AT); Robert Liska, Schleinbach (AT); Patrick Knaack, Vienna (AT); Moritz Mitterbauer, Vienna (AT)

(73) Assignee: Ivoclar Vivadent AG, Schaan (LI)

( * ) Notice: Subject to any disclaimer, the term of this patent is extended or adjusted under 35 U.S.C. 154(b) by 57 days.

(21) Appl. No.: 16/329,987

(22) PCT Filed: Sep. 4, 2017

(86) PCT No.: PCT/EP2017/072099
§ 371 (c)(1),
(2) Date: Mar. 1, 2019

(87) PCT Pub. No.: WO2018/046438
PCT Pub. Date: Mar. 15, 2018

(65) Prior Publication Data
US 2019/0194362 A1    Jun. 27, 2019

(30) Foreign Application Priority Data
Sep. 7, 2016   (EP) ..................................... 16187716

(51) Int. Cl.
*C08F 2/50*     (2006.01)
*A61K 6/62*     (2020.01)
(Continued)

(52) U.S. Cl.
CPC .................. *C08F 2/50* (2013.01); *A61K 6/62* (2020.01); *A61K 6/887* (2020.01); *C08F 20/18* (2013.01);
(Continued)

(58) Field of Classification Search
CPC ... C08F 2/50; C08F 20/18; A61K 6/62; A61K 6/887; C08K 3/013; C08K 5/57; C08K 2201/011
See application file for complete search history.

(56) References Cited

U.S. PATENT DOCUMENTS 4,071,424 A      1/1978  Dart et al.
4,178,425 A  *  12/1979  Emmons .................. C04B 26/06
                                                            525/125

(Continued)

FOREIGN PATENT DOCUMENTS

CA      2019210 A1   12/1990
CA      2296227 A1    7/2000
(Continued)

OTHER PUBLICATIONS

B. Ganster, et al., "New Photocleavable Structures. Diacylgermane-Based Photoinitiators for Visible Light Curing," Macromolecules, 41, 2394-2400, 2008.
(Continued)

*Primary Examiner* — Jessica M Roswell
(74) *Attorney, Agent, or Firm* — Ann M. Knab; Thad McMurray

(57) ABSTRACT

Polymerizable compositions are described which contain, as photoinitiator, at least one acyltin compound according to the general formula (I):
(Continued)

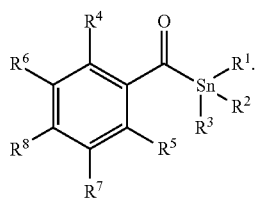

formula (I)

16 Claims, 1 Drawing Sheet

(51) Int. Cl.
  C08K 3/013 (2018.01)
  C08F 20/18 (2006.01)
  A61K 6/887 (2020.01)
  C08K 5/57 (2006.01)

(52) U.S. Cl.
  CPC ........... C08K 3/013 (2018.01); C08K 5/57 (2013.01); *C08K 2201/011* (2013.01)

(56) References Cited

U.S. PATENT DOCUMENTS

| | | | |
|---|---|---|---|
| 4,457,818 | A | 7/1984 | Denyer et al. |
| 4,525,256 | A | 6/1985 | Martin |
| 6,043,361 | A | 3/2000 | Evans et al. |
| 6,344,556 | B1 | 2/2002 | Evans et al. |
| 6,479,592 | B2 | 11/2002 | Rheinberger et al. |
| 7,585,901 | B2 | 9/2009 | Moszner et al. |
| 2003/0021565 | A1 | 1/2003 | Khudyakov et al. |
| 2005/0282700 | A1 | 12/2005 | Feldman et al. |
| 2008/0076847 | A1 | 3/2008 | Moszner et al. |
| 2008/0277814 | A1 | 11/2008 | Moszner et al. |
| 2009/0239967 | A1 | 9/2009 | Moszner et al. |

FOREIGN PATENT DOCUMENTS

| | | |
|---|---|---|
| CA | 2397140 A1 | 7/2001 |
| CA | 2930267 A1 | 5/2015 |

OTHER PUBLICATIONS

T.N. Mitchell et al., "Some further studies on acyltrimethylstannanes," Journal of Organometallic Chemistry, 439, 127-138, 1992.
J.-P. Bouillon et al., "Synthesis and Intramolecular Aldol Reactions of 1,6- and 1,7-Bis(acylsilanes)," Eur. J. Org. Chem., 1571-1580, 1999.
J.-P. Fouassier et al., "Radiation Curing in Polymer Science and Technology, vol. II," Photoinitiating Systems, Elsevier Applied Science, 1993.
A.G. Brook, et al., "Synthesis of Silyl and Germyl Ketones," J. Amer. Chem. Soc., vol. 89, pp. 431-434, 1967.
Nakamura, T. et al., "Nucleophilic addition of tri-2-furylgermane to aldehydes and α,β-unsaturated carbonyl compounds in the presence of a catalytic amount of base," Tetrahedron 57, pp. 9827-9836, 2001.
Moszner, N. et al., "Benzoyl germanium derivatives as novel visible light photoinitiators for dental materials," Dental Materials, 24, pp. 901-907, 2008.
Quintard, J-P. et al., "Some aspects of the reactivity of a-chloro ethoxymethyltributain: reductive etherification of aromatic aldehydes and demonstration of formyltributyltin during the hydrolysis reaction," J. Organomet. Chem., vol. 251, 175-187, 1983.
Moszner, N. et al., "Benzoylgermanium Derivatives as Novel Visible-Light Photoinitiators for Dental Composites," Macromolecular Materials and Engineering, vol. 294, pp. 877-886, 2009.
Moszner, N. et al., "Photoinitiators for direct adhesive restorative materials," Basics and Applications of Photopolymerization Reactions, 91-112, 2010.
Peddle, G. J. D., "The Preparation and Properties of α-tin Ketones," Journal of Organometallic Chemistry, vol. 14, pp. 139-147, 1968.

\* cited by examiner

POLYMERIZABLE COMPOSITIONS WITH ACYLTIN PHOTOINITIATORS

CROSS-REFERENCE TO RELATED APPLICATIONS

This application is a National Stage application of International patent application PCT/EP2017/072099 filed on Sep. 4, 2017, which claims priority to European patent application No. 16187716.2 filed on Sep. 7, 2016, the disclosures of which are incorporated herein by reference in their entirety.

FIELD OF INVENTION

The present invention relates to polymerizable compositions which contain an acyltin compound as polymerization initiator. The compositions are particularly suitable for the preparation of adhesives, coatings, cements, composites, shaped parts such as rods, plates, discs or lenses and in particular of dental materials and materials for the stereolithographic production of shaped parts.

The photoinitiator used plays a decisive role in the curing of photopolyreactive resins. Upon irradiation with UV or visible light, it absorbs light and forms the polymerization-initiating species. In the case of radical polymerization these are free radicals. The photoinitiators are divided into two classes based on the chemical mechanism of radical formation.

BACKGROUND OF THE INVENTION

Norrish type I photoinitiators form free radicals upon irradiation by unimolecular bond cleavage. Upon irradiation, Norrish type II photoinitiators undergo a bimolecular reaction, wherein the photoinitiator in the excited state reacts with a second molecule, the coinitiator, and the polymerization-initiating radicals form by electron and proton transfer. Type I and type II photoinitiators are used for UV light curing; to date, apart from bisacyldialkylgermanium compounds, almost exclusively type II photoinitiators are used for the visible light range.

UV curing is characterized by a high reaction rate and is frequently used for the coatings of different substrates such as e.g. wood, metal or glass. Thus for example in EP 1 247 843 A2 a UV-curing coating material is described, in which type I photoinitiators such as diethoxyphenylacetophenone or acyl- or bisacylphosphine oxides are used.

WO 01/51533 A1 describes a UV-curing wood-coating material, in which likewise acylphosphine oxides, α-hydroxyalkylphenones or α-dialkoxyacetophenones are used as photoinitiators. Above all, transparent coatings with low layer thickness can be produced with UV curing due to the low wavelength of the UV light. The limits of UV curing are reached with pronounced shading or pigmentation, in filled systems and with greater layer thicknesses. Such photopolyreactive resins with clearly reduced transparency cure only incompletely with UV light.

If greater through-curing depths are required, such as for example in the curing of light-curing dental filling materials, visible light is used for irradiation. The photoinitiator system most frequently used for this is a combination of an α-diketone with an amine coinitiator, as described e.g. in GB 1 408 265.

Dental compositions in which this photoinitiator system is used are disclosed e.g. in U.S. Pat. No. 4,457,818 or U.S. Pat. No. 4,525,256, wherein preferably camphorquinone is used as α-diketone. Camphorquinone has an absorption maximum at a wavelength of 468 nm. As a result camphorquinone displays a strong yellow colouring, with the disadvantage that materials initiated with camphorquinone/amine often have a yellowness after curing as the initiator system is not completely bleached (N. Moszner, R. Liska, Photoinitiators for direct adhesive restorative materials, In: Basics and Applications of Photopolymerization Reactions, Vol. 1; Fouassier, J.-P., Allonas, X., Eds., Research Signpost, Kerala, 2010, 93-114). This bleaching behaviour is very disadvantageous in particular in the case of bright white shades of the fully polymerized material. In addition, when used in acidic adhesives, camphorquinone/amine systems have the disadvantage that the radical-forming amine component is protonated and is thereby partially deactivated for radical formation.

The use of germanium compounds as photoinitiators is known. Bisacyldialkylgermanium compounds in particular are efficient Norrish type I photoinitiators for curing in the blue light range (B. Ganster, U. K. Fischer, N. Moszner, R. Liska, New photocleavable structures, Diacylgerman-based photoinitiators for visible light curing, Macromolecules 41 (2008) 2394-2400; N. Moszner, U. K. Fischer, B. Ganster, R. Liska, V. Rheinberger, Benzoyl germanium derivatives as novel visible light photoinitiators for dental materials Dent. Mater. 24 (2008) 901-907; N. Moszner, F. Zeuner, I. Lamparth, U. K. Fischer, Benzoylgermanium derivatives as novel visible-light photoinitiators for dental composites, Macromol. Mater. Eng. 294 (2009) 877-886).

EP 1 905 413 A1 and EP 1 905 415 A1 disclose mono-, bis- and triacylgermanium compounds which are suitable as photoinitiators for curing dental materials with visible light. Their synthesis is costly and is carried out starting from expensive dialkylgermanium dihalides using the dithiane protective-group technique and purification using column chromatography.

From EP 2 103 297 A1 suitable acylgermanium compounds which contain several germanium atoms are known as photoinitiators.

WO 2015/067815 A1 discloses bis(germyl) ketones of the formula $R^1R^2R^3Ge(CO)GeR^4R^5R^6$ and processes for the preparation thereof. These bis(germyl) ketones are also intended to be suitable as photoinitiators for dental materials.

SUMMARY OF THE INVENTION

The object of the invention is to provide polymerizable compositions which can be cured with light in the visible range, which are characterized by high reactivity and good curing characteristics as well as good bleaching behaviour and which can be cured in particular by visible light in the long-wave range of the visible spectrum.

BRIEF DESCRIPTION OF THE DRAWINGS

Further advantages, details and features result from the subsequent description of several exemplary embodiments of the invention with the help of the drawings, wherein.

DETAILED DESCRIPTION

Figure 1:
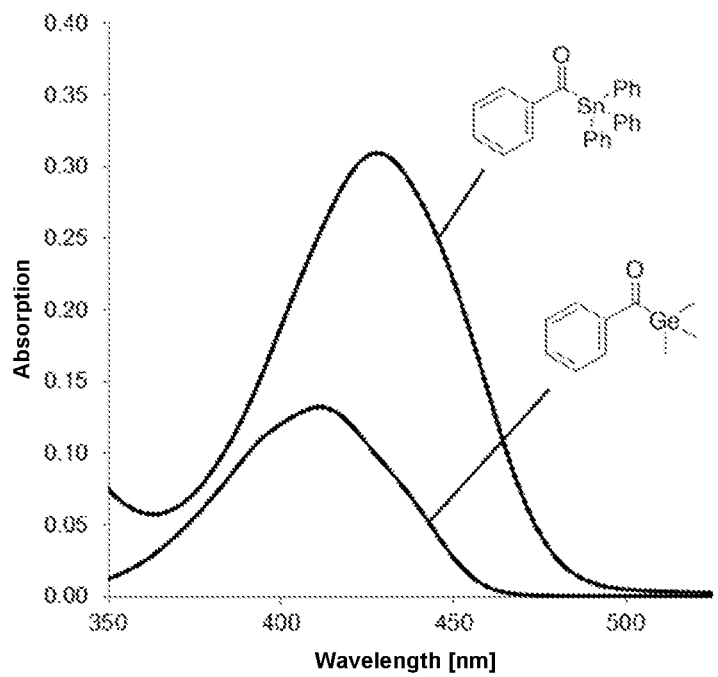
FIG. 1 shows an absorption spectrum of an acetonitrile solution of benzoyltriphenyltin (BtPhSn) with a concentration of 1.0 mmol/l in comparison with benzoyltrimethylgermanium(BtMGe).

The objects of the invention are achieved by polymerizable compositions which contain, as photoinitiator, at least one acyltin compound according to the general formula (I)

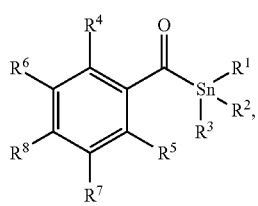

formula (I)

in which $R^1$, $R^2$, $R^3$ independently of each other are in each case a group of the formula (II)

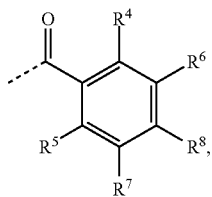

formula (II)

an aromatic $C_{6-30}$ radical, which can be substituted by one or more cyclic, branched or preferably linear $C_{1-20}$-alkyl, $C_{1-20}$-alkenyl, $C_{1-20}$-alkoxy, $C_{1-20}$-alkylthio or $C_{1-20}$-alkenoxy radicals, wherein the named substituents themselves can be interrupted one or more times by —O—, —S —or —NR$^9$- and/or can be substituted by one or more radically polymerizable groups and/or radicals $R^{10}$, a cyclic, branched or preferably linear $C_{1-20}$-alkyl, $C_{1-20}$-alkenyl, $C_{1-20}$-alkoxy, $C_{1-20}$-alkylthio, $C_{1-20}$-alkenoxy or $C_{1-20}$-acyloxy radical, which can be interrupted one or more times by —O—, —S —or —NR$^9$- and/or can be substituted by one or more radically polymerizable groups and/or radicals $R^{10}$, or a benzoyloxy radical, —H, trimethylsilyl, —OH, halogen or —CN, wherein $R^1$ and $R^2$, taken together, can also represent a double-bonded oxygen or sulfur atom or, together with the Sn atom to which they are bonded, can form an aliphatic saturated or unsaturated ring which in addition to the Sn atom contains 2 to 6 carbon atoms and optionally one or more oxygen atoms, wherein one or more carbon atoms can be substituted by a double-bonded oxygen atom and/or the ring can be fused with an aromatic ring, $R_4$, $R^5$, $R^6$, $R^7$, $R^8$ independently of each other are in each case —H, a cyclic, branched or preferably linear $C_{1-20}$-alkyl, $C_{1-20}$-alkenyl, $C_{1-20}$-alkyloxy or $C_{1-20}$-alkenoxy radical, which can be interrupted one or more times by —O—, —S —or —NR$^9$- and/or can be substituted by one or more radically polymerizable groups and/or radicals $R^{10}$, —OR$^9$, halogen, —SR$^9$, —N(R$^9$)$_2$, —CF$_3$, —CN, —NO$_2$, —COOR$^9$ or —CONHR$^9$, $R^9$ is —H or a cyclic, branched or preferably linear $C_{1-20}$-alkyl or $C_{1-20}$-alkenyl radical and $R^{10}$ is —OH, —C$_x$F$_{2x+1}$ with x=1 to 20 or —[Si(CH$_3$)$_2$]$_y$-CH$_3$ with y =1 to 20.

If several radicals of one type, e.g. several radicals $R^4$, $R^5$, $R^6$ etc., are present, these can be different or preferably identical. Preferred radically polymerizable groups, which can be present as substituents in the radicals, are vinyl, styryl, acrylate (CH$_2$=CH—CO—O—), methacrylate (CH$_2$=C(CH$_3$)—CO—O—), acrylamide (CH$_2$=CH—CO—NR'— with R'=H or C$_1$-C$_8$-alkyl), methacrylamide (CH$_2$=C(CH$_3$)—CO—NH—), particularly preferably (meth)acrylate, methacrylamide and/or N-alkylacrylamide. The radicals preferably bear 0 to 3 and in particular 0 to 1 radically polymerizable groups. In non-cyclic radicals the polymerizable groups are preferably arranged terminally.

Formula (I) and the remaining formulae shown herein cover all stereoisomeric forms as well as mixtures of different stereoisomeric forms, such as e.g. racemates. The formulae cover only those compounds that are compatible with the chemical valence theory.

The indication that a radical can be interrupted by a heteroatom such as O is to be understood to mean that the O atoms are inserted into the carbon chain or the carbon ring of the radical, i.e. are bordered on both sides by carbon atoms. The number of heteroatoms is therefore at least 1 smaller than the number of carbon atoms, and the heteroatoms cannot be terminal. In the case of hydrocarbon radicals which contain carbon atoms and heteroatoms, the number of heteroatoms is always smaller than the number of carbon atoms, without taking into account substituents.

Halogen (abbreviated to hal) in particular stands for F, Cl, Br or I, preferably for F, Cl and quite particularly preferably for Cl.

Preferred are in particular acyltin compounds according to the general formula (I) in which, in each case independently of each other, $R^1$,$R^2$,$R^3$ independently of each other are in each case a group of the formula (II), an aromatic $C_{6-15}$ radical, which can be substituted by one or more branched or preferably linear $C_{1-12}$-alkyl or $C_{1-12}$-alkoxy radicals, wherein the named substituents themselves can be interrupted one or more times by —O— and/or can be substituted by one or more radically polymerizable groups and/or —OH; a branched or preferably linear $C_{1-12}$-alkyl, $C_{1-12}$-alkenyl, $C_{1-12}$-alkoxy, $C_{1-12}$-alkylthio or $C_{1-12}$-acyloxy radical, which can be interrupted one or more times by —O— and/or can be substituted by one or more radically polymerizable groups and/or —OH, a benzoyloxy radical, trimethylsilyl, —OH, halogen or —CN, wherein $R^1$ and $R^2$, taken together, can also represent a double-bonded oxygen or sulfur atom or, together with the Sn atom to which they are bonded, can form an aliphatic saturated or unsaturated ring which in addition to the Sn atom contains 2 to 6, in particular 4, carbon atoms and optionally one or more, in particular 2, oxygen atoms, wherein one or more, in particular 2, carbon atoms can be substituted by a double-bonded oxygen atom and/or the ring can be fused with an aromatic, in particular six-membered, ring, $R^4$,$R^5$,$R^8$ independently of each other are in each case -H, a branched or preferably linear $C_{1-12}$-alkyl, $C_{1-12}$-alkenyl, $C_{1-12}$-alkyloxy or $C_{1-12}$-alkenoxy radical, which can be interrupted one or more times by —O— and/or can be substituted by one or more radically polymerizable groups and/or —OH; or —OR$^9$, halogen, —SR$^9$, —N(R$^9$)$_2$, —CF$_3$, —CN or —NO$_2$, $R^6$,$R^7$ independently of each other are in each case —H or —F or a branched or preferably linear $C_{1-12}$-alkyl, $C_{1-12}$-alkenyl, $C_{1-12}$-alkyloxy or $C_{1-12}$-alkenoxy radical, which can be interrupted one or more times by —O— and/or can be substituted by one or more radically polymerizable groups and/or —OH, and R$^9$ is —H or methyl.

Particularly preferred are acyltin compounds of the formula (I) in which, in each case independently of each other, R$^1$,R$^2$,R$^3$ independently of each other are in each case a group of the formula (II), phenyl, trimethylphenyl, a branched or preferably linear C$_{1-8}$-alkyl, C$_{1-12}$-alkylthio or C$_{1-12}$-acyloxy radical, a benzoyloxy, vinyl or methacryloyl radical, trimethylsilyl, —OH, —Cl or —CN, wherein R$^1$ and R$^2$, taken together, can also represent a double-bonded oxygen or sulfur atom or, together with the Sn atom to which they are bonded, can form a dioxastannepin ring, wherein one or preferably two carbon atoms of the dioxastannepin ring can be substituted by a double-bonded oxygen atom and/or the ring can be fused with a benzene ring, R$^4$,R$^5$,R$^8$ independently of each other are in each case —H, a branched or preferably linear C$_{1-8}$-alkyl radical, which can be interrupted by 1 to 3 O atoms and/or can be substituted by vinyl, or —OR$^9$, halogen, —SR$^9$, —N(R$^9$)$_2$, —CF$_3$, —CN or —NO$_2$, R$^6$,R$^7$ independently of each other are in each case —H, —F or a branched or preferably linear C$_{1-8}$-alkyl radical, which can be interrupted by 1 to 3 O atoms and/or can be substituted by vinyl, and R$^9$ is —H or methyl.

Quite particularly preferred are acyltin compounds of the formula (I) in which, in each case independently of each other, R$^1$,R$^2$,R$^3$ independently of each other are in each case a group of the formula (II), phenyl, a linear C$_1$-C$_8$-alkyl radical or trimethylsilyl, R$^4$,R$^5$,R$^8$ independently of each other are in each case —H, methyl, —OR$^9$ or —F, R$^6$,R$^7$ independently of each other are in each case —H or —F and R$^9$ is —H or methyl.

Compounds in which all the variables each have one of the preferred meanings defined above are particularly preferred.

Some of the acyltin compounds of the general formula (I) used according to the invention are already known from the state of the art. The synthesis of the monoacylstannanes can be carried out for example by lithiation of triorganotin chloride and subsequent reaction with acid chloride (cf. G. J. D. Peddle, J. Organometal. Chem. 14 (1968) 139-147):

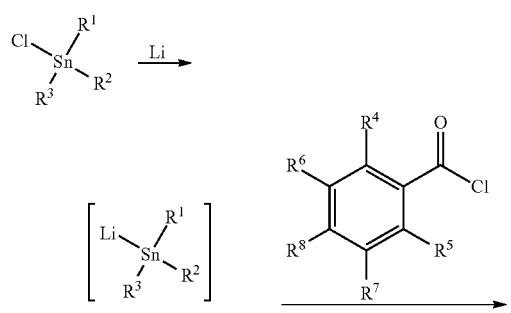

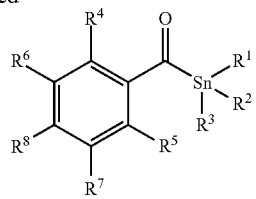

SPECIFIC EXAMPLE

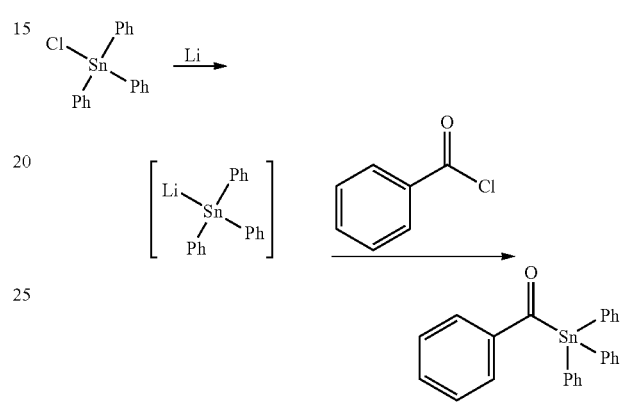

A further possibility for the synthesis of acyltin compounds is a synthesis variant in which firstly an Sn Grignard compound is prepared, and this is then reacted with an aldehyde (cf. J. P. Quintard, B. Elissondo, D. Mouko-Mpegna, J. Organomet. Chem. 251 (1983) 175-187):

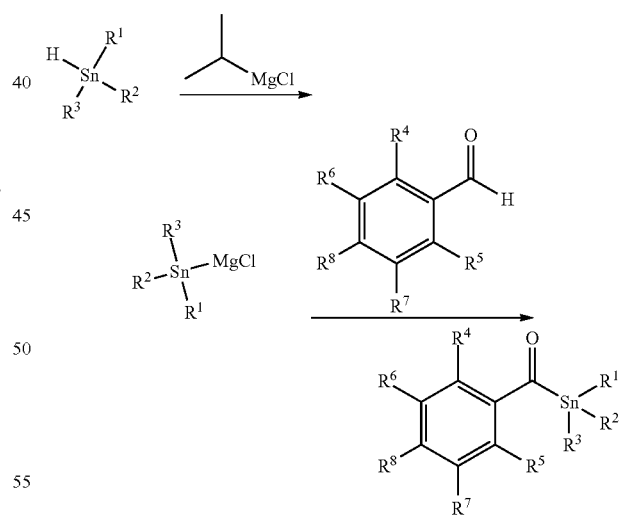

Specific Example

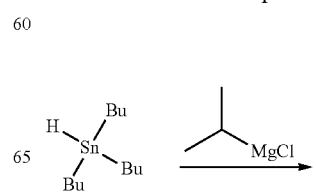

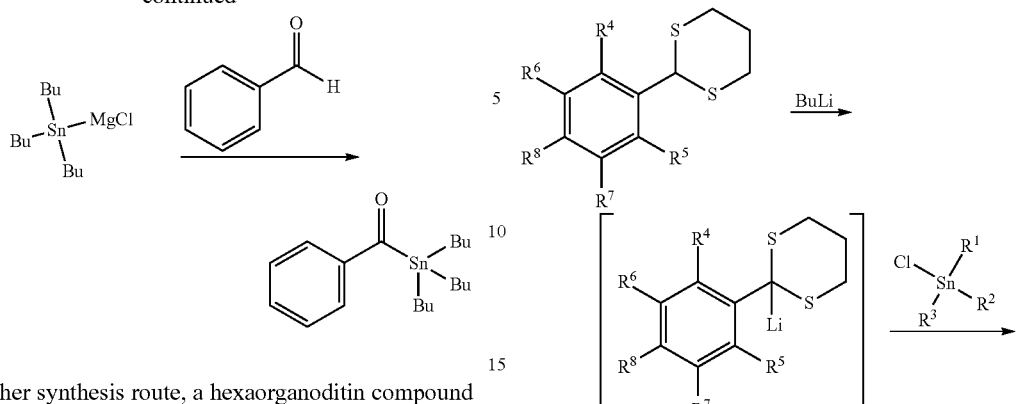

In a further synthesis route, a hexaorganoditin compound is used as starting material (cf. T. N. Mitchell, K. Kwetkat, J. Organomet. Chem. 439 (1992) 127-138.):

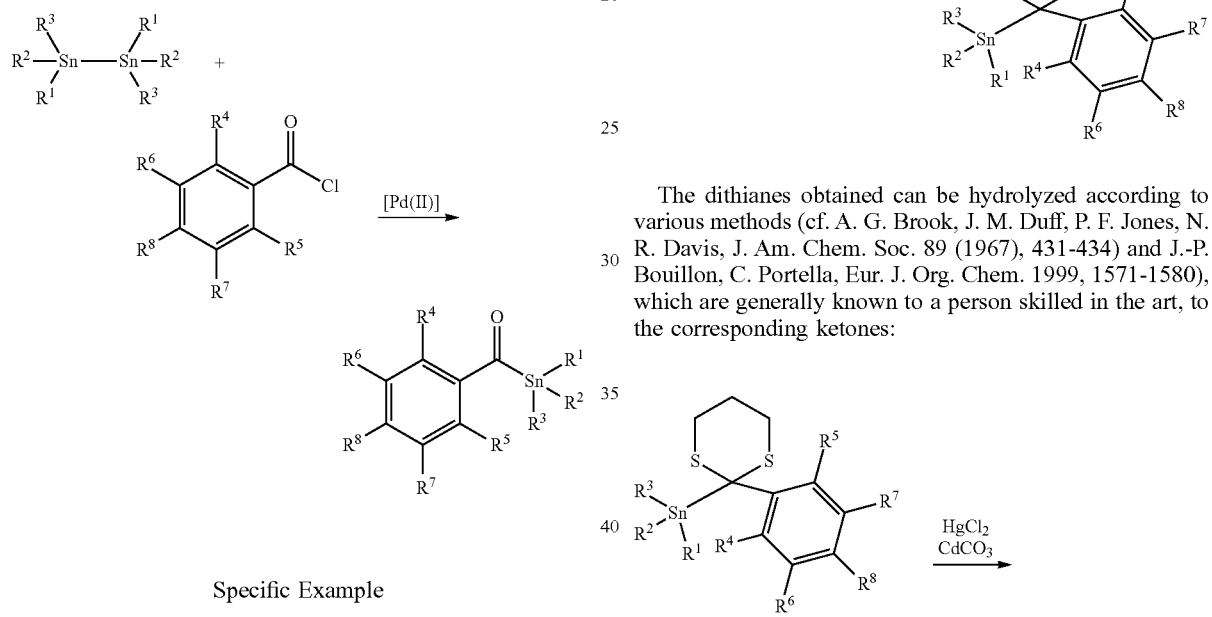

Specific Example

Furthermore, acyltin compounds can be synthesized by reacting a carbanion which is obtained from 1,3-dithianes with tin chlorides (cf. A. G. Brook, J. M. Duff, P. F. Jones, N. R. Davis, J. Am. Chem. Soc. 89 (1967), 431-434):

The dithianes obtained can be hydrolyzed according to various methods (cf. A. G. Brook, J. M. Duff, P. F. Jones, N. R. Davis, J. Am. Chem. Soc. 89 (1967), 431-434) and J.-P. Bouillon, C. Portella, Eur. J. Org. Chem. 1999, 1571-1580), which are generally known to a person skilled in the art, to the corresponding ketones:

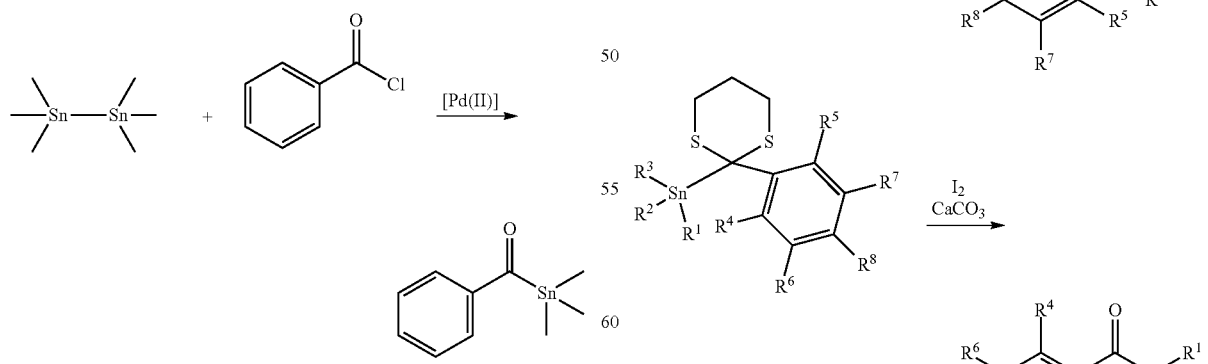

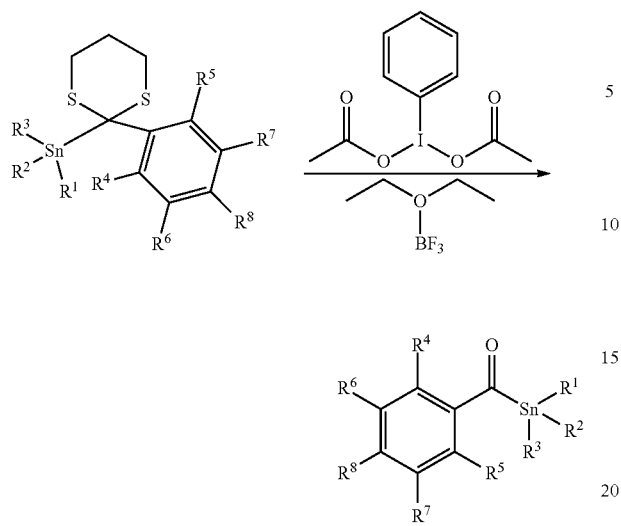

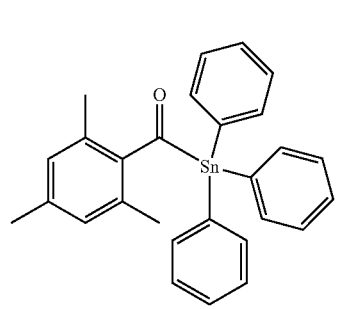

mesityl(triphenylstannyl)methanone

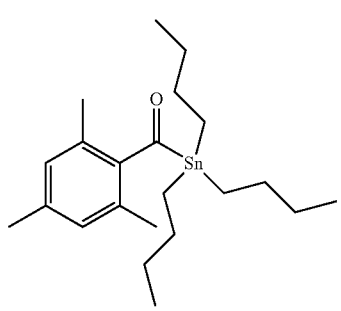

mesityl(tributylstannyl)methanone

Analogously to the corresponding germanium compounds, acyltin compounds can also be obtained by oxidation of hydroxyl groups (cf. T. Nakamura, H. Yorimitsu, H. Shinokubo, K. Oshima, Tetrahedron 57 (2001) 9827-9836):

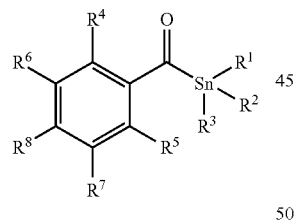

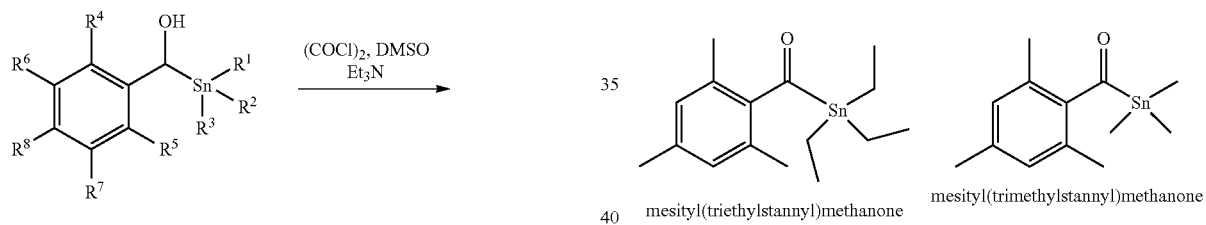

mesityl(triethylstannyl)methanone    mesityl(trimethylstannyl)methanone

Specific examples of particularly preferred compounds are:

Monoacylstannanes

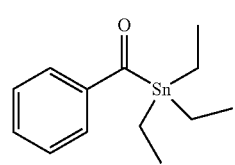    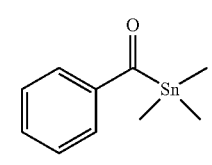

phenyl(triethylstannyl)methanone    phenyl(trimethylstannyl)methanone

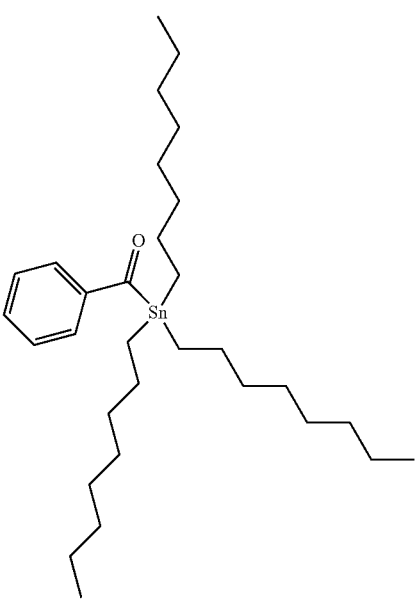

phenyl(trioctylstannyl)methanone

-continued

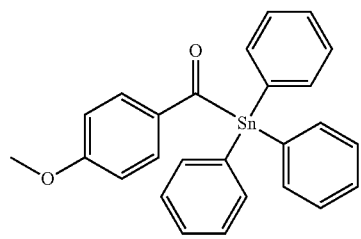

4-methoxyphenyl(triphenylstannyl)methanone

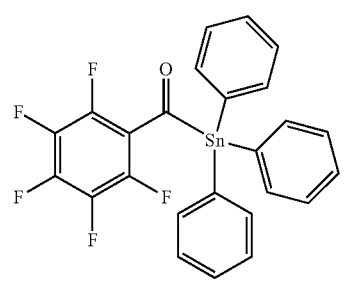

perfluorophenyl(triphenylstannyl)methanone

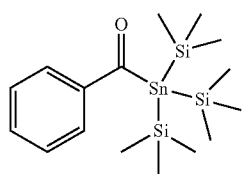

phenyl(tris(trimethylsilyl)stannyl)methanone

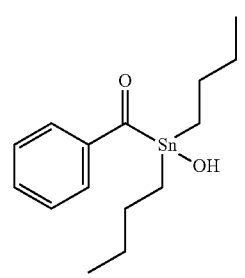

(dibutyl(hydroxyl)stannyl)(phenyl)methanone

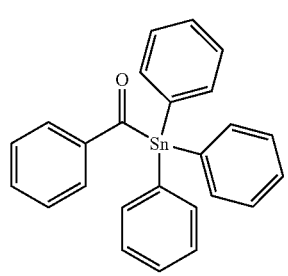

phenyl(triphenylstannyl)methanone

-continued

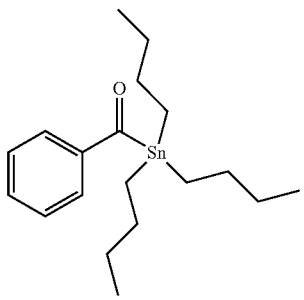

phenyl(tributylstannyl)methanone

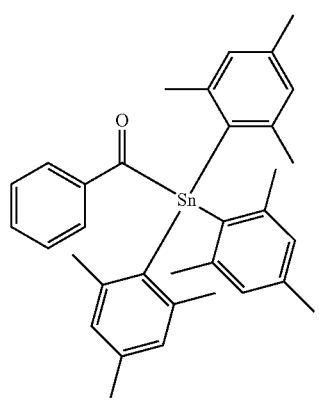

phenyl(trimesitylstannyl)methanone

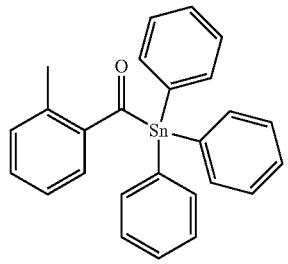

o-tolyl(triphenylstannyl)methanone

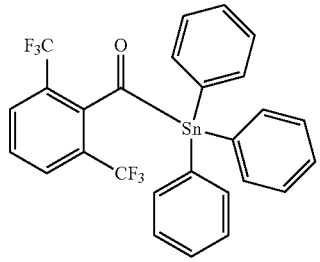

2,6-bis(trifluoromethyl)phenyl)(triphenylstannyl)methanone

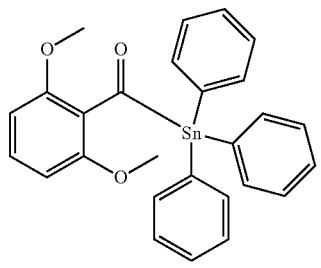

2,6-dimethoxyphenyl)(triphenylstannyl)-methanone

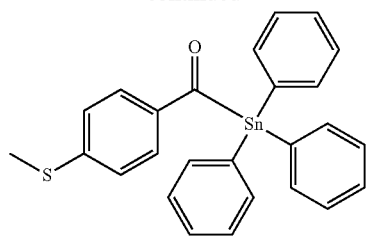

4-(methylthio)phenyl(triphenylstannyl)-
methanone

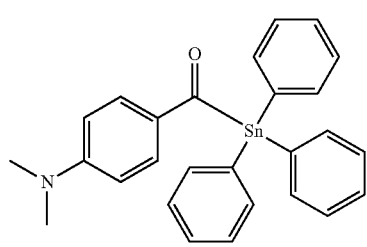

4-(dimethylamino)phenyl)(triphenylstannyl)-
methanone

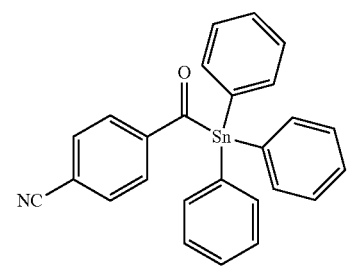

4-((triphenylstannyl)carbonyl)-
benzonitrile

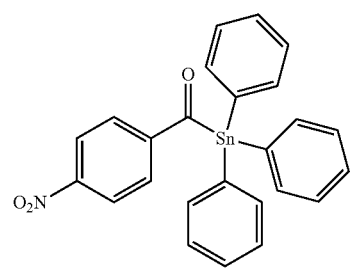

4-nitrophenyl(triphenylstannyl)methanone

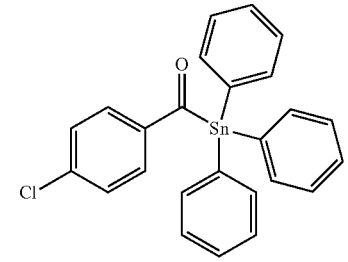

(4-chlorophenyl)(triphenylstannyl)methanone

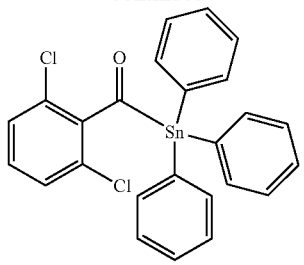

2,6-dichlorophenyl)(triphenylstannyl)methanone

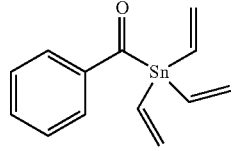

phenyl(trivinylstannyl)methanone

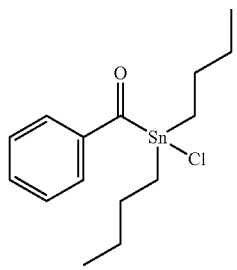

(dibutylchlorostannyl)(phenyl)methanone

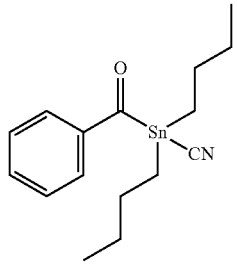

benzoyldibutylstannanecarbonitrile

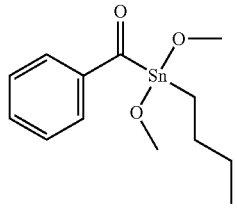

(butyldimethoxystannyl)(phenyl)methanone

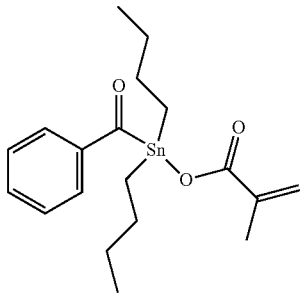

(benzoyldibutylstannyl)methacrylate

Diacylstannanes

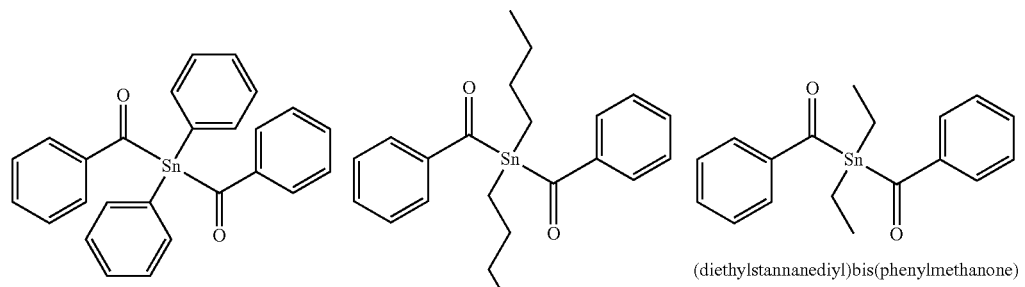

(diphenylstannanediyl)bis(phenyl-methanone)

(dibutylstannanediyl)bis(phenyl-methanone)

(diethylstannanediyl)bis(phenylmethanone)

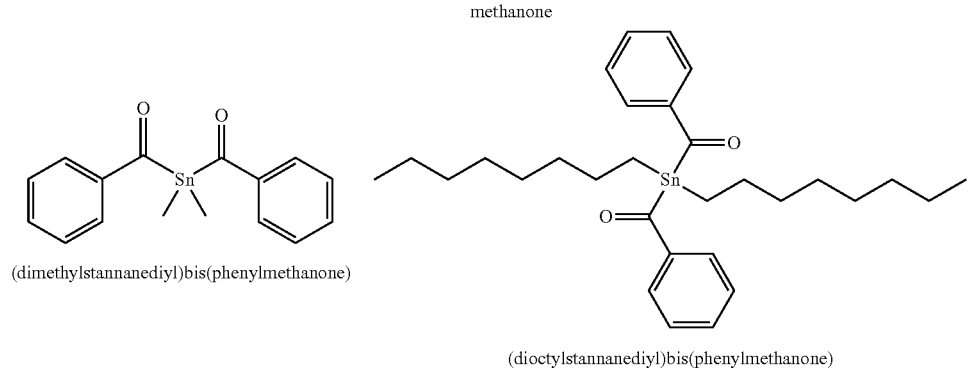

(dimethylstannanediyl)bis(phenylmethanone)

(dioctylstannanediyl)bis(phenylmethanone)

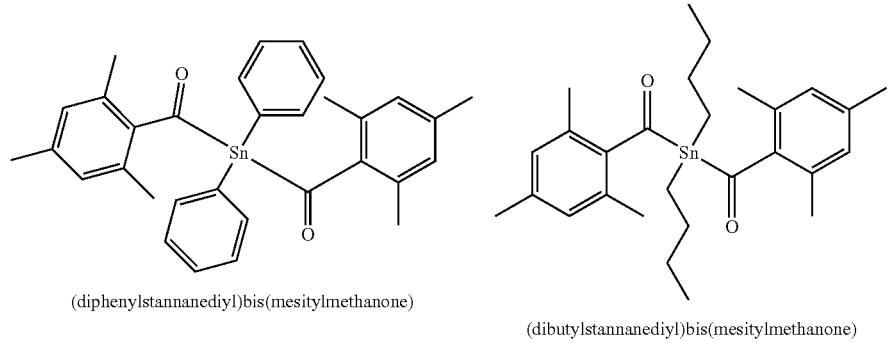

(diphenylstannanediyl)bis(mesitylmethanone)

(dibutylstannanediyl)bis(mesitylmethanone)

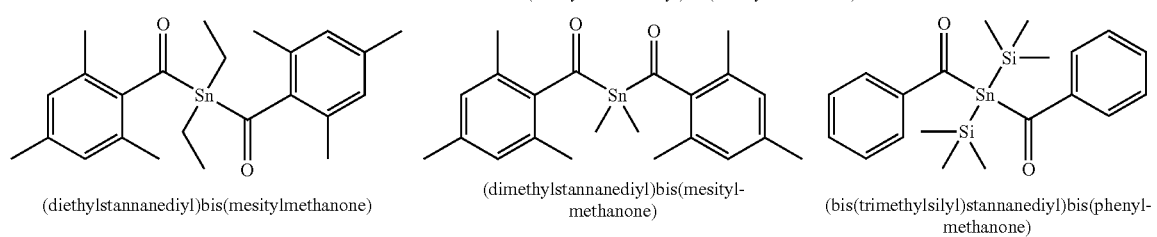

(diethylstannanediyl)bis(mesitylmethanone)

(dimethylstannanediyl)bis(mesityl-methanone)

(bis(trimethylsilyl)stannanediyl)bis(phenyl-methanone)

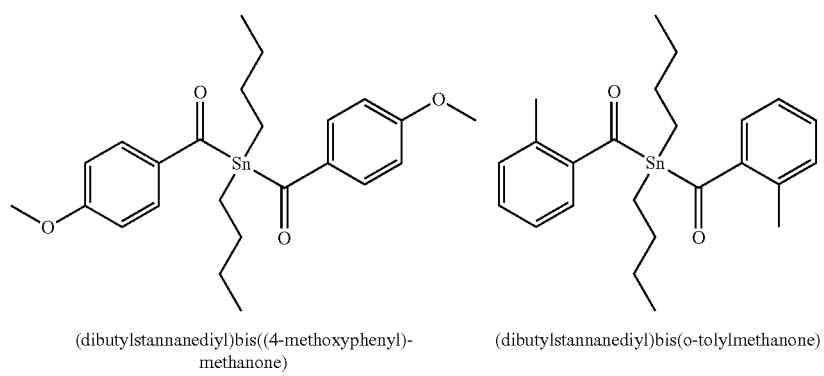

(dibutylstannanediyl)bis((4-methoxyphenyl)-methanone)

(dibutylstannanediyl)bis(o-tolylmethanone)

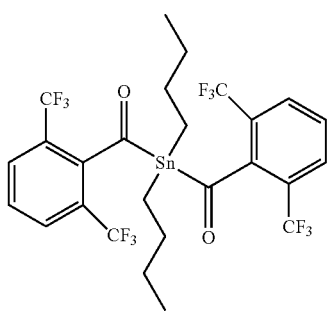

(dibutylstannanediyl)bis((2,6-bis(trifluoromethyl)phenyl)methanone)

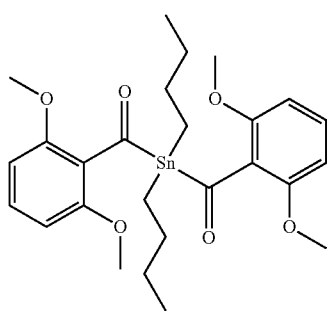

(dibutylstannanediyl)bis((2,6-dimethoxyphenyl)methanone)

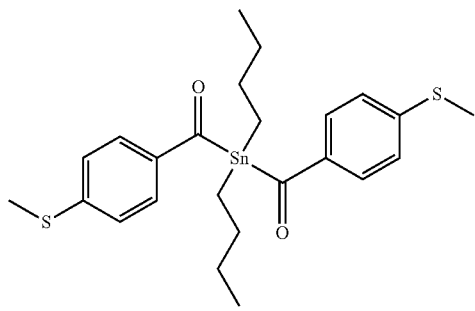

(dibutylstannanediyl)bis((4-methylthio)phenyl)methanone)

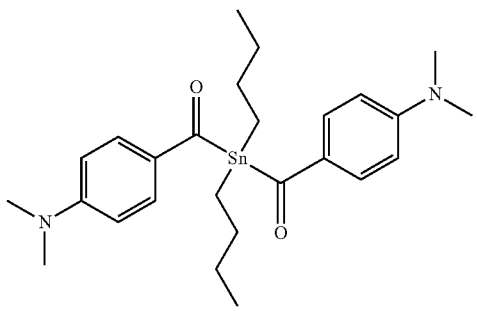

(dibutylstannanediyl)bis((4-(dimethylamino)phenyl)methanone)

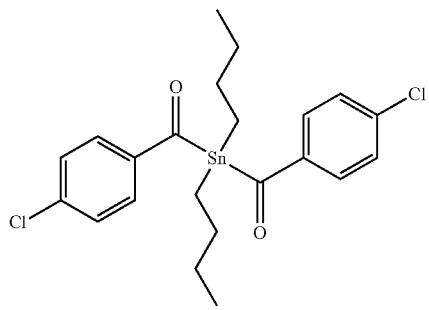

(dibutylstannanediyl)bis((4-chlorophenyl)methanone

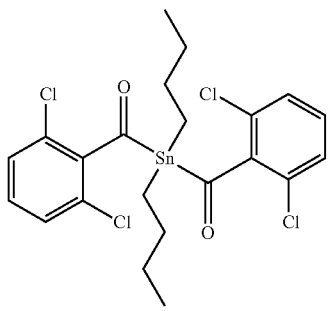

(dibutylstannanediyl)bis((2,6-dichlorophenyl)methanone)

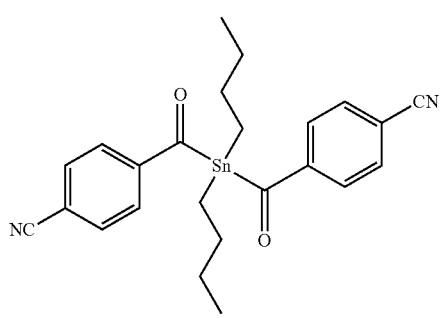

4'-((dibutylstannanediyl)bis(carbonyl))-dibenzonitrile

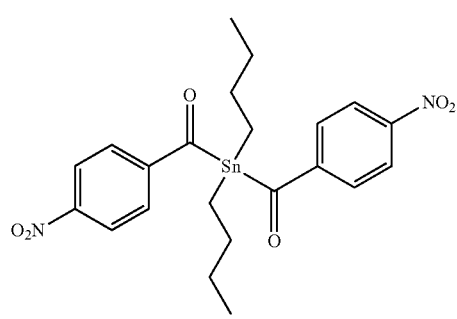

(dibutylstannanediyl)bis((4-nitrophenyl)methanone)

-continued
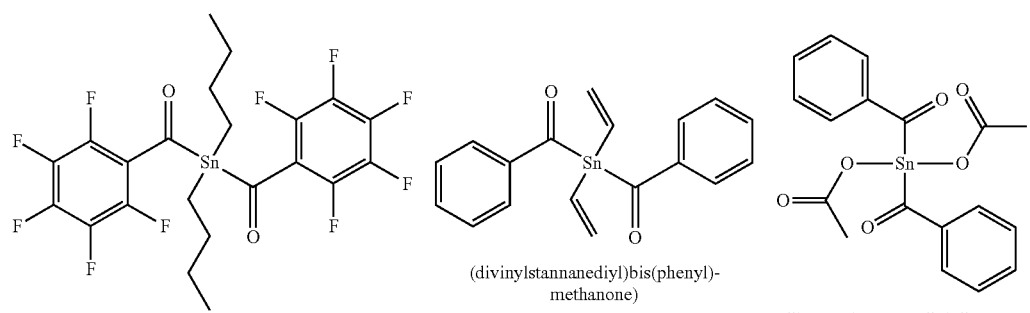
(dibutylstannanediyl)bis((perfluorophenyl)-methanone)
(divinylstannanediyl)bis(phenyl)-methanone)
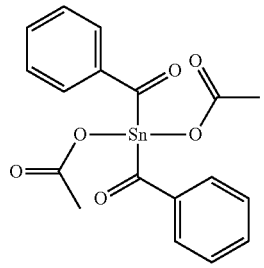
dibenzoylstannanediyl diacetate
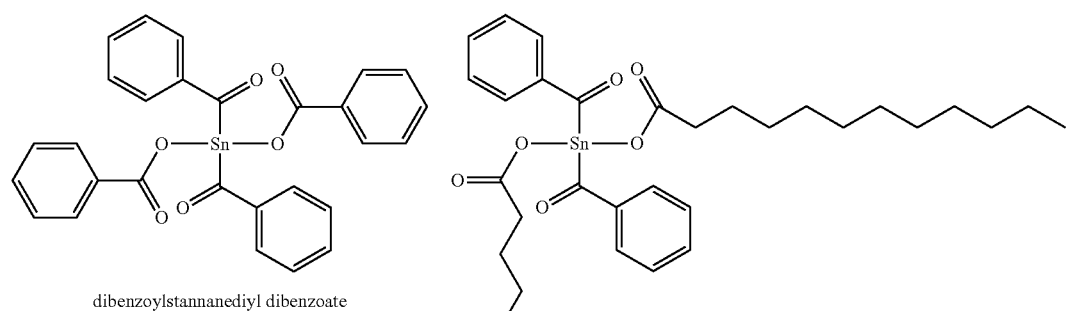
dibenzoylstannanediyl dibenzoate
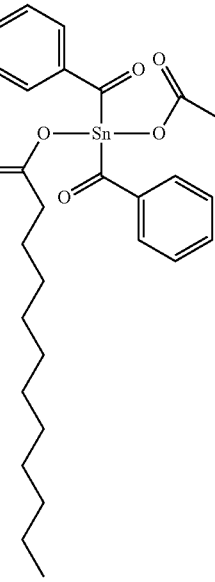
dibenzoylstannanediyl didodecanoate
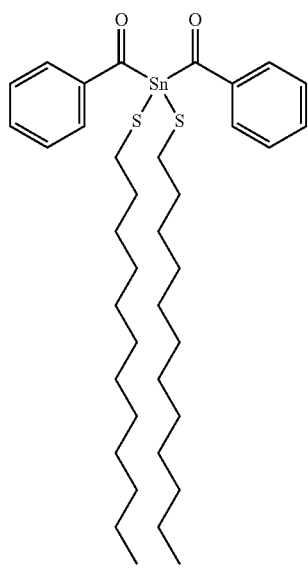
(bis(dodecylthio)stannanediyl)bis(phenyl-methanone)
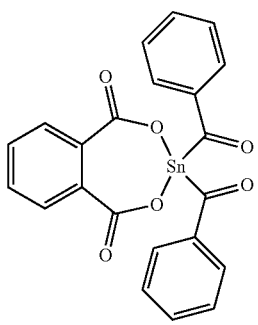
3,3-dibenzoylbenzo[e][1,3,2]dioxastannepin-1,5-dione
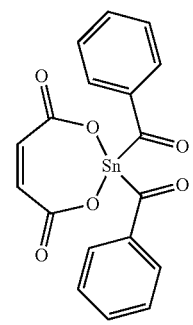
2,2-dibenzoyl-1,3,2-dioxastannepin-4,7-dione

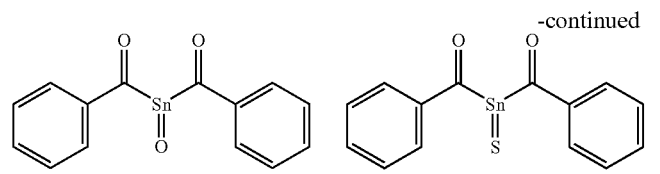

(oxostannanediyl)bis(phenylmethanone)  (thioxostannanediyl)bis(phenylmethanone)

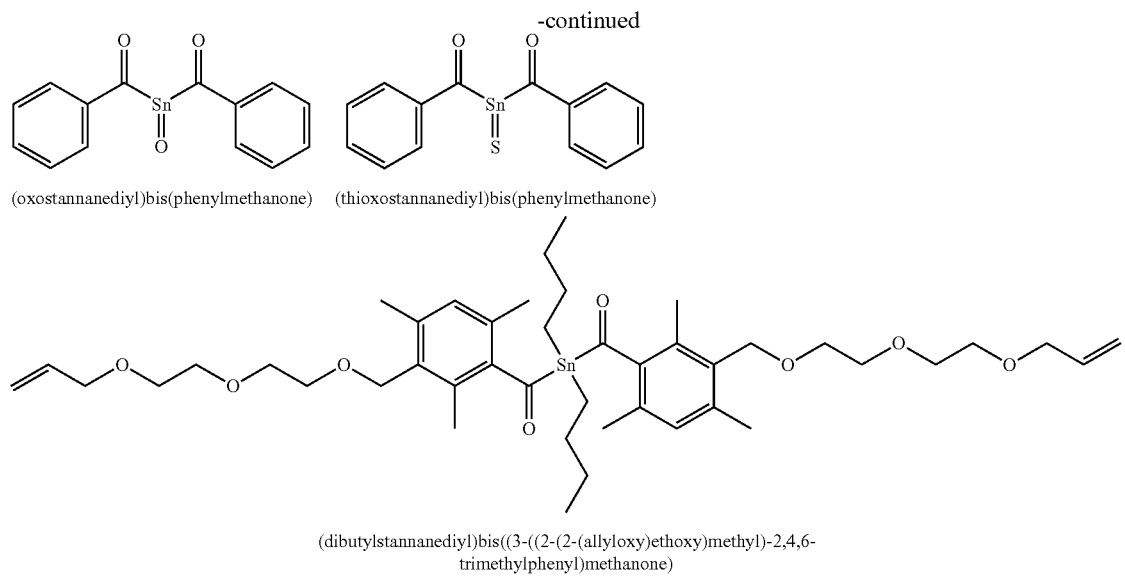

(dibutylstannanediyl)bis((3-((2-(2-(allyloxy)ethoxy)methyl)-2,4,6-trimethylphenyl)methanone)

Triacylstannanes

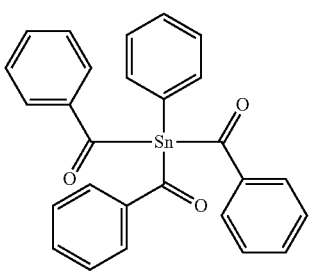

(phenylstannanetriyl)tris(phenyl-methanone)

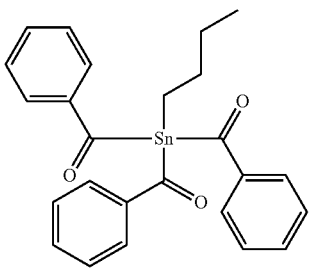

(butylstannanetriyl)tris(phenyl-methanone)

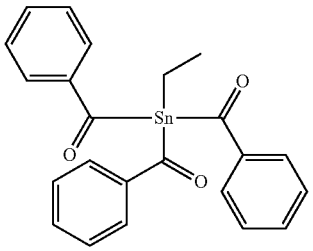

(ethylstannanetriyl)tris(phenyl-methanone)

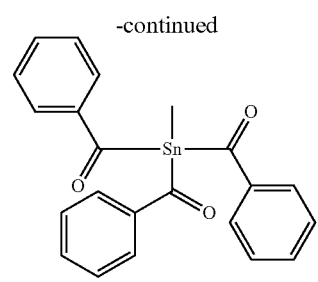

(methylstannanetriyl)tris(phenyl-methanone)

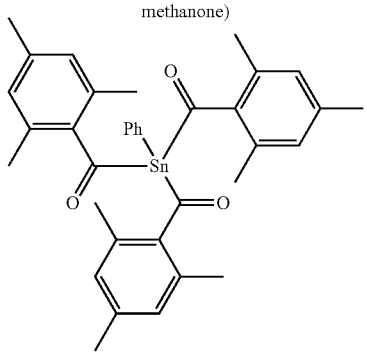

(phenylstannanetriyl)tris(mesityl-methanone)

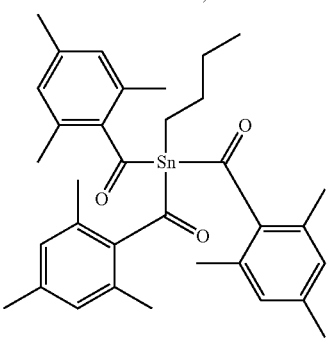

(butylstannanetriyl)tris(mesityl-methanone)

-continued

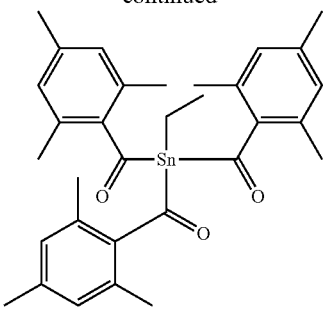

(ethylstannanetriyl)tris(mesityl-
methanone)

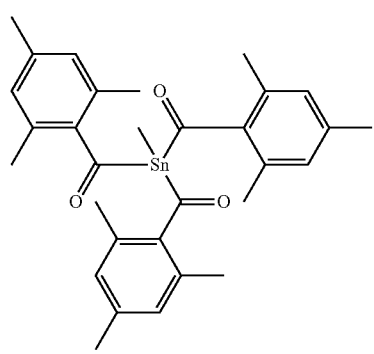

(methylstannanetriyl)tris(mesityl-
methanone)

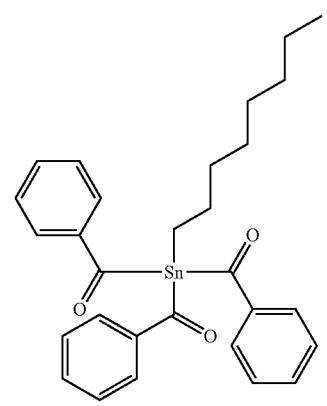

(octylstannanetriyl)tris(phenyl-
methanone)

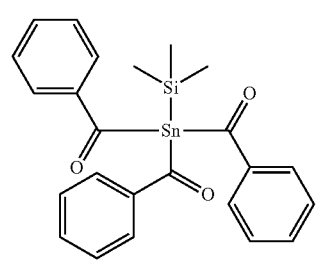

((trimethylsilyl)stannanetriyl)tris(phenyl-
methanone)

-continued

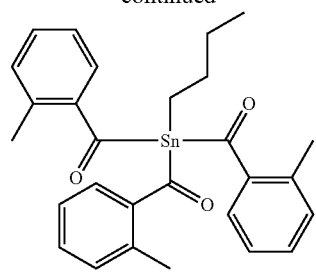

(butylstannanetriyl)tris(o-tolylmethanone)

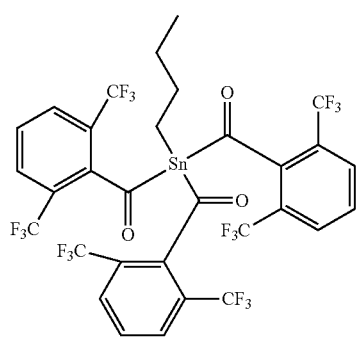

(butylstannanetriyl)tris((2,6-bis(trifluoromethyl)phenyl)methanone)

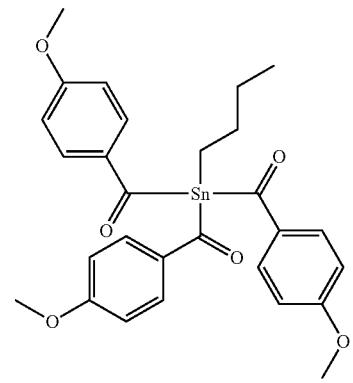
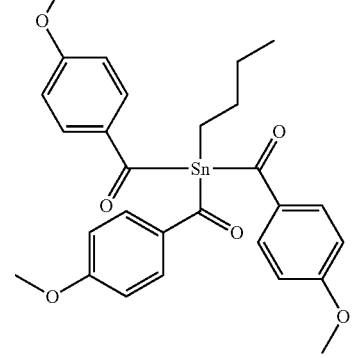
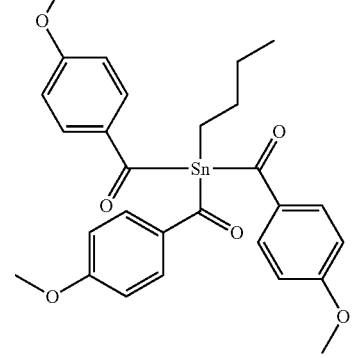

(butylstannanetriyl)tris((4-methoxyphenyl)methanone)

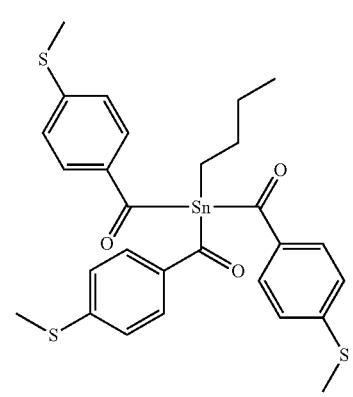

(butylstannanetriyl)tris((4-(methylthio)phenyl)methanone)

25
-continued

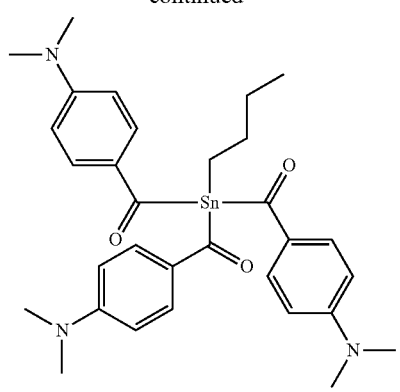

(butylstannanetriyl)tris((4-(dimethylamino)phenyl)methanone)

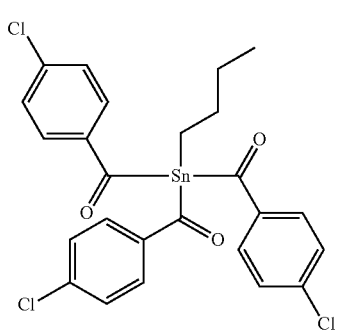

(butylstannanetriyl)tris((4-chlorophenyl)-
methanone)

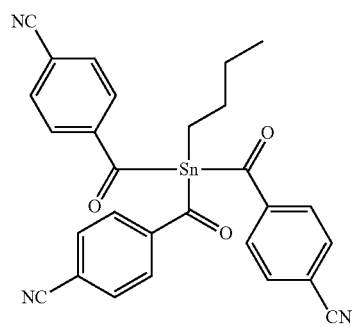

4,4',4''-((butylstannanetriyl)tris(carbonyl))-
tribenzonitrile

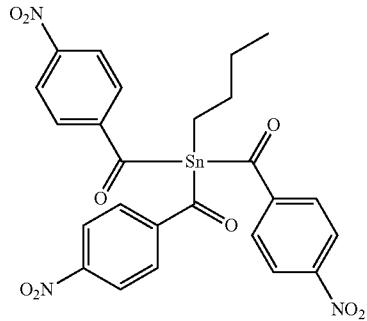

(butylstannanetriyl)tris((4-nitrophenyl)methanone)

26
Tetraacylstannanes

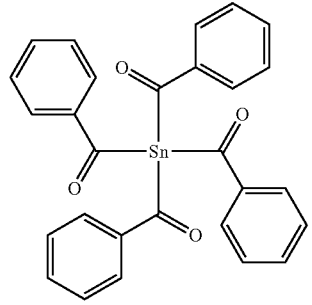

stannanetetrayltetra(phenylmethanone)

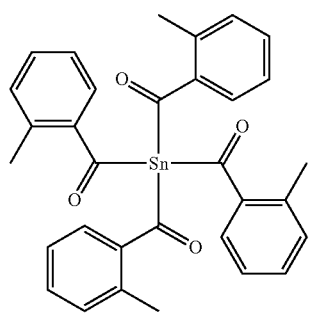

stannanetetrayltetrakis(o-tolylmethanone)

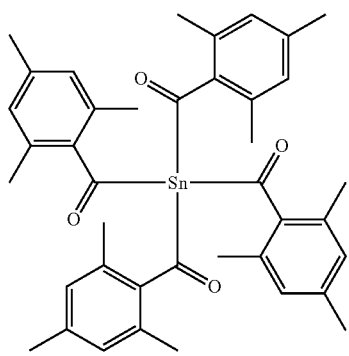

stannanetetrayltetrakis(mesityl-
methanone)

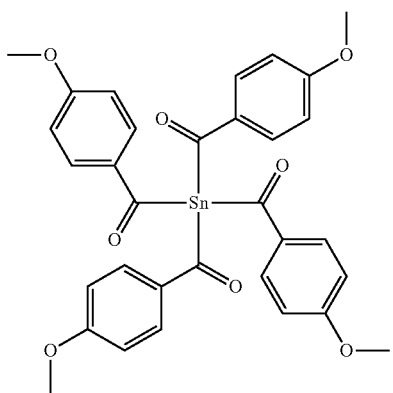

stannanetetrayltetrakis((4-
methoxyphenyl)methanone)

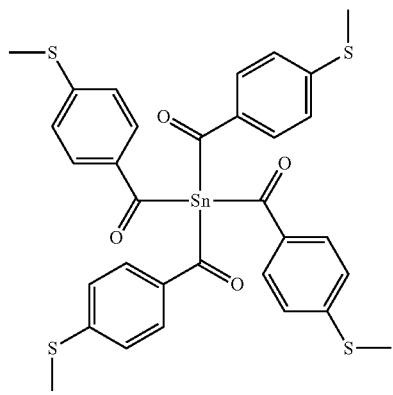

stannanetetrayltetrakis((4-(methylthio)phenyl)methanone)

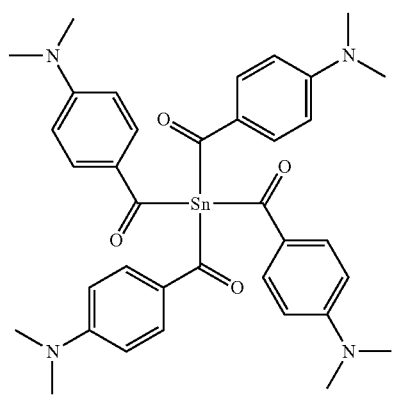

stannanetetrayltetrakis((4-(dimethylamino)phenyl)methanone)

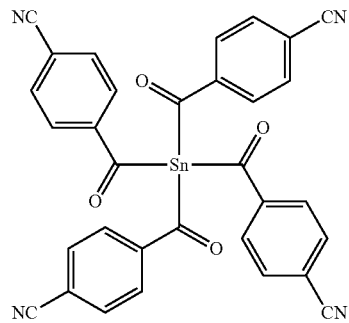

4,4′,4″,4‴-(stannanetetrayltetrakis(carbonyl))tetrabenzonitrile

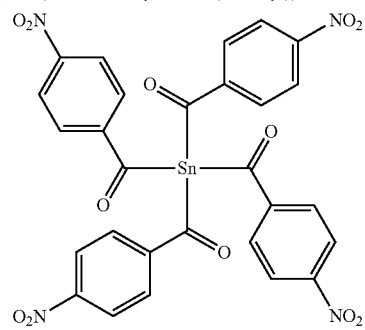

stannanetetrayltetrakis((4-nitrophenyl)methanone)

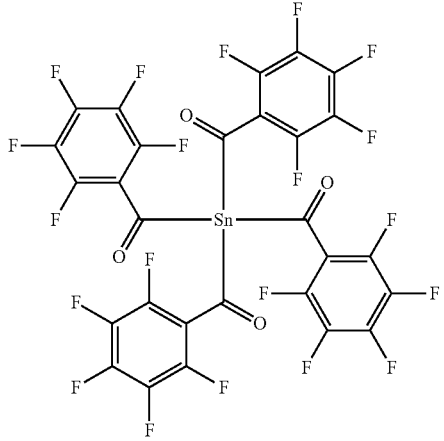

stannanetetrayltetrakis((perfluorophenyl)methanone)

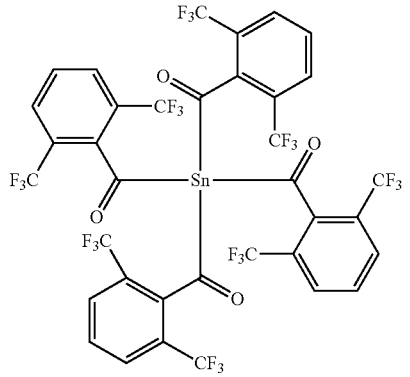

stannanetetrayltetrakis((2,6-bis(trifluoromethyl)phenyl)methanone)

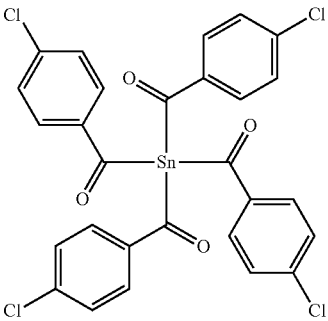

stannanetetrayltetrakis((4-chlorophenyl)methanone)

It was surprisingly found that the compounds of the formula (I) are outstandingly suitable as photoinitiators for polymerization and in particular for radical polymerization, particularly for initiating compositions based on the monomers defined below. The compounds of the formula (I) are relatively easily accessible and exhibit a very good polymerization-initiating effect and excellent bleaching behaviour. They are furthermore also suitable as photoinitiators for other polyreactions such as e.g. polyaddition.

The compounds of the formula (I) are particularly suitable for medical uses, for example for the production of bone cements and contact lenses, intraocular lenses or other medical shaped parts, such as e.g. hearing aid shells, cartilage implants and artificial tissue parts, and quite particularly for the preparation of dental materials such as adhesives, coatings, cements and composites. The acyltin compounds of the formula (I) are furthermore also suitable for the preparation of materials for the production of shaped parts by stereolithographic processes.

Moreover, the initiators of the formula (I) are suitable for a plurality of non-medical uses, such as for example for the production of shaped parts, e.g. rods, plates, discs or lenses etc., printing inks or paints, varnishes, adhesives, for the production of printing plates, integrated circuits, photoresists, soldering masks, inks for colour printers, as materials for holographic data storage, for the production of nanosized microelectromechanical elements, optical waveguides, shaped parts and for the optical production of information carriers. An important field of application is the use as photoinitiator in the stereolithographic production of technical shaped parts, e.g. of precision shaped parts and ceramic green bodies.

The compositions according to the invention preferably contain, relative to the total mass of the composition, 0.001 to 5 wt.-%, particularly preferably 0.01 to 1.0 wt.-% acyltin compound of the formula (I).

In addition to the acyltin compound of the formula (I), the compositions preferably also contain a polymerizable binder. Preferred binders are radically and/or cationically polymerizable monomers and/or prepolymers, particularly preferably radically polymerizable monomers, radically polymerizable prepolymers or a mixture thereof.

Mono- or multifunctional (meth)acrylates or mixtures thereof are particularly suitable as radically polymerizable binders. By monofunctional (meth)acrylic compounds are meant compounds with one, by multifunctional (meth) acrylic compounds are meant compounds with two or more, preferably 2 to 3, polymerizable groups.

Examples in this respect are methyl, ethyl, hydroxyethyl, butyl, benzyl, tetrahydrofurfuryl or isobornyl (meth)acrylate, bisphenol A di(meth)acrylate, Bis-GMA (an addition product of methacrylic acid and bisphenol A diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, as well as glycerol di- and trimethacrylate, 1,4-butanediol di(meth)acrylate, 1,10-decanediol di(meth)acrylate or 1,12-dodecanediol di(meth)acrylate. Compositions which contain at least one radically polymerizable monomer with 2 or more, preferably 2 to 3, radically polymerizable groups are particularly preferred. Polyfunctional monomers have cross-linking properties.

Hydrolytically stable diluting monomers such as hydrolytically stable mono(meth)acrylates can also be used as radically polymerizable binders, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as e.g. N-ethylacrylamide, N,N-dimethacrylamide, N-(2-hydroxyethyl)acrylamide or N-methyl-N-(2-hydroxyethyl)acrylamide, or N-monosubstituted methacrylamides, such as e.g. N-ethylmethacrylamide or N-(2-hydroxyethyl)methacrylamide and also N-vinylpyrrolidone or allyl ether. Preferred examples of hydrolytically stable cross-linking monomers are urethanes of 2-(hydroxymethyl)acrylic acid and diisocyanates, such as 2,2,4-trimethylhexamethylene diisocyanate or isophorone diisocyanate, cross-linking pyrrolidones, such as e.g. 1,6-bis(3-vinyl-2-pyrrolidonyl)-hexane, or commercially available bisacrylamides, such as methylene or ethylene bisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction from the corresponding diamines with (meth)acrylic acid chloride.

Known low-shrinkage radically ring-opening polymerizable monomers such as e.g. mono- or multifunctional vinylcyclopropanes or bicyclic cyclopropane derivatives (cf. DE 196 16 183 C2 or EP 1 413 569 A1) or cyclic allyl sulfides (cf. U.S. Pat. No. 6,043,361 or U.S. Pat. No. 6,344,556) can furthermore also be used as radically polymerizable binders and can in addition also be used in combination with the di(meth)acrylate cross-linkers listed above. Suitable ring-opening polymerizable monomers are such vinylcyclopropanes such as 1,1-di(ethoxycarbonyl)- or 1,1-di(methoxycarbonyl)-2-vinylcyclo-propane or the esters of 1-ethoxycarbonyl- or 1-methoxycarbonyl-2-vinylcyclopropanecarboxylic acid with ethylene glycol, 1,1,1-trimethylolpropane, 1,4-cyclohexanediol or resorcinol. Suitable bicyclic cyclopropane derivatives are 2-(bicyclo[3.1.0]hex-1-yl) acrylic acid methyl or ethyl esters or their disubstitution products in the 3-position, such as (3,3-bis(ethoxycarbonyl) bicyclo[3.1.0]hex-1-yl)acrylic acid methyl or ethyl ester. Suitable cyclic allyl sulfides are the addition products of 2-(hydroxymethyl)-6-methylene-1,4-dithiepane or 7-hydroxy-3-methylene-1,5-dithiacyclooctane with 2,2,4-trimethylhexamethylene 1,6-diisocyanate or an asymmetrical hexamethylene diisocyanate trimer (e.g. Desmodur® VP LS 2294 from Bayer AG).

Formulations based on vinyl esters, vinyl carbonates and vinyl carbamates are also preferred as radically polymerizable monomers. In addition, styrene, styrene derivatives or divinylbenzene, unsaturated polyester resins and allyl compounds or radically polymerizable polysiloxanes, which can be prepared from suitable methacrylic silanes such as e.g. 3-(methacryloyloxy)propyltrimethoxysilane and are described e.g. in DE 199 03 177 C2, can be used as monomers.

Furthermore, mixtures of the previously named monomers with radically polymerizable, acid-group-containing monomers which are also called adhesive monomers can also be used as radically polymerizable binders. Preferred acid-group-containing monomers are polymerizable carboxylic acids, such as maleic acid, acrylic acid, methacrylic acid, 2-(hydroxymethyl)acrylic acid, 4-(meth) acryloyloxyethyltrimellitic acid anhydride, 10-methacryloyloxydecylmalonic acid, N-(2-hydroxy-3-methacryloyloxypropyl)-N-phenylglycine or 4-vinylbenzoic acid.

Radically polymerizable phosphonic acid monomers, in particular vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[2-dihydroxyphosphoryl)-ethoxymethyl]-acrylic acid ethyl or 2,4,6-trimethylphenyl ester, are also suitable as adhesive monomers.

Furthermore, acidic polymerizable phosphoric acid esters, in particular 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol pentamethacryloyloxyphosphate, 10-methacryloyloxydecyl dihydrogen phosphate, dipentaerythritol pentamethacryloyloxyphosphate, phosphoric acid mono-(1-acryloyl-piperidin-4-yl) ester, 6-(methacrylamido)hexyl dihydrogen phosphate and 1,3-bis-(N-acryloyl-N-propyl-amino)-propan-2-yl dihydrogen phosphate, are suitable as adhesive monomers.

In addition, polymerizable sulfonic acids, in particular vinylsulfonic acid, 4-vinylphenylsulfonic acid or 3-(methacrylamido)propylsulfonic acid, are suitable as adhesive monomers.

Thiol-ene resins which contain mixtures of mono- or multifunctional mercapto compounds and di- or multifunctional unsaturated monomers, above all allyl or norbornene compounds, are particularly suitable as binders curable by polyaddition.

Examples of mono- or multifunctional mercapto compounds are o-, m- or p-dimercaptobenzene and esters of thioglycol- or 3-mercaptopropionic acid with ethylene, propylene or butylene glycol, hexanediol, glycerol, trimethylolpropane or pentaerythritol.

Examples of di- or multifunctional allyl compounds are esters of allyl alcohol with di- or tricarboxylic acids such as malonic, maleic, glutaric, succinic, adipic, sebacic, phthalic, terephthalic or gallic acid as well as mono- or trifunctional allyl ethers such as e.g. diallyl ether, α,ω-bis[allyloxy]alkane, resorcinol or hydroquinone diallyl ether as well as pyrogallol triallyl ether, or other compounds such as e.g. 1,3,5-triallyl-1,3,5-triazine-2,4,6-(1H,3H,5H)-trione, tetraallylsilane or tetraallylorthosilicate.

Examples of di- or multifunctional norbornene compounds are Diels-Alder addition products of cyclopentadiene or furan with di- or multifunctional (meth)acrylates, as well as esters and urethanes of 5-norbornene-2-methanol or 5-norbornen-2-ol with di- or polycarboxylic acids, such as e.g. malonic, maleic, glutaric, succinic, adipic, sebacic, phthalic, terephthalic or gallic acid, or di- or polyisocyanates, such as hexamethylene diisocyanate or its cyclic trimer, 2,2,4-trimethylhexamethylene diisocyanate, toluene diisocyanate or isophorone diisocyanate.

In addition to acyltin compounds of the general formula (I), the compositions according to the invention can advantageously additionally also contain known photoinitiators (cf. J. P. Fouassier, J. F. Rabek (Ed.), Radiation Curing in Polymer Science and Technology, Vol. II, Elsevier Applied Science, London and New York 1993) for the UV or visible range, such as e.g. benzoin ether, dialkyl benzil ketals, dialkoxyacetophenones, acyl or bisacyl phosphine oxides, α-diketones such as 9,10-phenanthrenequinone, diacetyl, furil, anisil, 4,4'-dichlorobenzil and 4,4'-dialkoxybenzil and camphorquinone. Combinations with Norrish type I photoinitiators, above all acyl or bisacyl phosphine oxides, such as for example the commercially available compounds 2,4,6-trimethylbenzoyldiphenyl phosphine oxide and bis(2,4,6-trimethylbenzoyl)phenyl phosphine oxide, are highly suitable, and monoacyltrialkyl-, diacyldialkylgermanium, triacylalkyl- and tetraacylgermanium compounds, such as e.g. benzoyltrimethylgermanium, dibenzoyldiethylgermanium or bis(4-methoxybenzoyl)diethylgermanium and tetrabenzoylgermanium, are particularly suitable. Mixtures of different photoinitiators can also be used. Initiator combinations of the acyltin compounds of the general formula (I) can also be used which additionally contain aromatic diaryliodonium or triarylsulfonium salts, for example the commercially available compounds 4-octyloxyphenyl-phenyl-iodonium hexafluoroantimonate or isopropylphenyl-methylphenyl-iodonium tetrakis(pentafluorophenyl)borate.

The compositions according to the invention can furthermore also contain azo compounds such as 2,2'-azobis(isobutyronitrile) (AIBN) or azobis-(4-cyanovaleric acid), or peroxides such as dibenzoyl peroxide, dilauroyl peroxide, Cert-butyl peroctoate, Cert-butyl perbenzoate or di-(cert-butyl) peroxide in addition to the acyltin compounds of the general formula (I) for dual curing. To accelerate the initiation by means of peroxides, combinations with aromatic amines can also be used. Redox systems which have already proved successful are: combinations of benzoyl peroxide with amines such as N,N-dimethyl-p-toluidine, N,N-dihydroxyethyl-p-toluidine, p-dimethylaminobenzoic acid ethyl ester or structurally related systems. In addition, redox systems consisting of peroxides and reducing agents such as e.g. ascorbic acid, barbiturates or sulfinic acids or combinations of hydroperoxides with reducing agents and catalytic metal ions such as e.g. a mixture of cumene hydroperoxide, a thiourea derivative and copper(II) acetylacetonate are also suitable for dual curing.

According to the invention, compositions are preferred which contain one or more fillers, preferably organic or inorganic particulate fillers. Particulate materials with an average particle size of 1 nm to 10 μm, preferably of 5 nm to 5 μm, are preferably used as fillers. The term "average particle size" refers here in each case to the volume average.

Preferred inorganic particulate fillers, in particular for the dental field, are amorphous spherical nanoparticulate fillers based on oxides, such as pyrogenic silica or precipitated silica, $ZrO_2$ and $TiO_2$ or mixed oxides of $SiO_2$, $ZrO_2$ and/or $TiO_2$ with an average particle size of 10 to 200 nm, mini fillers such as quartz, glass ceramic or glass powder with an average particle size of 0.2 to 5 μm and x-ray opaque fillers such as ytterbium trifluoride or nanoparticulate tantalum(V) oxide or barium sulfate. In addition, fibrous fillers such as nanofibres, glass fibres, polyamide or carbon fibres can also be used.

For non-dental uses, in addition to the above-named materials, homo- and/or copolymers, preferably poly((meth)acrylate)s, vinyl polymers, preferably polystyrene or polyvinyl acetate, or condensation polymers, preferably polyester, also come into consideration as fillers. These fillers are preferably used as powder with an average particle size between 0.5 and 100 μm. They are partially soluble in the monomer. Inorganic fillers such as e.g. $CaCO_3$, talc, $TiO_2$, $CaSO_4$, silicates, glass, carbon powder or carbon fibres or metal powder based on Al, Zn, Cu or Ni can furthermore also be used for non-dental uses.

Additionally, the compositions according to the invention can, if necessary, contain further additives, such as e.g. stabilizers, UV absorbers, dyes or pigments, and solvents, such as e.g. water, ethanol, acetone or ethyl acetate, or slip additives.

The materials according to the invention preferably contain:
 (a) 0.001 to 5 wt.-% acyltin compound(s) of the general formula (I),
 (b) 10 to 99.999 wt.-% radically polymerizable binder,
 (c) 0 to 85 wt.-% filler and
 (d) 0 to 70 wt.-% additive(s).

Unless otherwise indicated, all percentages relate to the total mass of the material.

Materials which are particularly suitable as dental cements preferably contain:
 (a) 0.001 to 5 wt.-% acyltin compound(s) of the general formula (I),
 (b) 10 to 50 wt.-% radically polymerizable binder,
 (c) 40 to 70 wt.-% filler and
 (d) 0 to 5 wt.-% additive(s).

Materials which are particularly suitable as dental composites preferably contain:
 (a) 0.001 to 5 wt.-% acyltin compound(s) of the general formula (I),
 (b) 10 to 40 wt.-% radically polymerizable binder, (c) 50 to 85 wt.-% filler and
(d) 0 to 5 wt.-% additive(s).

Materials which are particularly suitable as dental coating materials preferably contain:
(a) 0.001 to 5 wt.-% acyltin compound(s) of the general formula (I),
(b) 10 to 99.989 wt.-% radically polymerizable binder,
(c) 0 to 20 wt.-% nanoparticulate fillers,
(d) 0.01 to 2 wt.-% additive(s) and
(e) 0 to 70 wt.-% solvent.

Materials which are particularly suitable as dental adhesives preferably contain:
(a) 0.001 to 5 wt.-% acyltin compound(s) of the general formula (I),
(b) 0 to 98.989 wt.-% radically polymerizable binder,
(c) 0 to 20 wt.-% nanoparticulate fillers,
(d) 0.01 to 2 wt.-% additive,
(e) 0 to 50 wt.-% solvent and
(f) 1 to 20 wt.-% radically polymerizable adhesive monomer.

Materials which are particularly suitable for stereolithography or 3D printing preferably contain:
(a) 0.001 to 5 wt.-% acyltin compound(s) of the general formula (I),
(b) 0 to 99 wt.-% radically polymerizable binder,
(c) 0 to 80 wt.-% filler(s) and
(d) 0 to 10 wt.-% additive(s).

Materials which are particularly suitable as coatings preferably contain:
(a) 0.001 to 5 wt.-% acyltin compound(s) of the general formula (I),
(b) 20 to 99 wt.-% radically polymerizable binder,
(c) 0 to 20 wt.-% dye(s) and/or pigment(s) and
(d) 0 to 10 wt.-% further additive(s).

Materials which are particularly suitable as printing inks preferably contain:
(a) 0.001 to 5 wt.-% acyltin compound(s) of the general formula (I),
(b) 20 to 95 wt.-% radically polymerizable binder,
(c) 1 to 20 wt.-% dye(s) and/or pigment(s) and
(d) 0 to 10 wt.-% further additive(s).

The compositions according to the invention are suitable for the preparation of photopolymerizates and as composites, cements, coating materials, primers or adhesives. They are particularly suitable for uses in the medical field, above all as dental materials such as filling composites, fixing cements, adhesives, prosthesis materials, veneering materials, as well as for the production of crowns, inlays or coatings.

The dental materials are suitable for intraoral application by the dentist to restore damaged teeth, i.e. for therapeutic application, e.g. as dental cements, filling composites and veneering materials. However, they can also be used extraorally, for example in the production or repair of dental restorations, such as prostheses, artificial teeth, inlays, onlays, crowns and bridges.

Furthermore, the materials according to the invention are suitable for medical use in surgery, e.g. in tissue regeneration, for the production of hearing aids or in ophthalmology for the production of intraocular lenses or contact lenses.

In technical applications, the compositions according to the invention can be used in stereolithography or in 3D printing for the production of shaped bodies, prototypes or green bodies, in the field of coatings or in microelectronics, e.g. in photoresist technology or nanoimprint lithography. A particularly preferred use of the materials according to the invention is in the field of 3D printing of ceramic or metal powders by means of processes based on lithography. The photopolymer prepared according to the invention represents the sacrificial structure in the sintering process here. Due to the relatively long-wave absorption maximum of the compounds of the formula (I) according to the invention, ceramics such as e.g. zirconium oxides, carbides and nitrides, e.g. based on silicon, and even metal powders, e.g. stainless steel or tool steels, can also be printed.

Moreover, the compositions according to the invention and the polymerizates prepared therefrom are also suitable as varnishes or coatings on various surfaces, e.g. as decorative coatings and protective coatings on wood, paper, cardboard and in particular plastic, ceramic or metal. The relatively long-wave absorption maximum of the compounds of the formula (I) according to the invention offers particular advantages in particular for the through-curing depth of pigmented or filled systems, for example in the area of ink-jet processes. Furthermore, the compositions according to the invention and the polymerizates prepared therefrom can also be used as adhesives for bonding a wide variety of materials or for the preparation of shaped bodies by moulding, pressing, rapid prototyping or 3D printing.

The invention is explained in more detail below with reference to examples.

Example 1

Synthesis of Benzoyltriphenyltin (BtPhSn)

Using a glove box, 1 eq. (1.69 g) triphenyltin chloride and 3 eq. (0.09 g) lithium foil were weighed out into separate Schlenk flasks and 10 ml anhydrous THF was then added to each of these flasks. The reaction vessels were connected to an inert-gas manifold in a laboratory under orange light and 0.05 eq. (0.03 g) naphthalene (as catalyst) was subsequently added to the lithium suspension. The suspension was placed in an ultrasound bath for 20 minutes at room temperature (RT) and then stirred intensively for a further 30 minutes, whereupon the suspension rapidly changed to a dark colour. The triphenyltin chloride solution was then added dropwise by means of a syringe and septum to the lithium suspension at RT over a period of 20 minutes, whereby the reaction mixture briefly decoloured again. Stirring was continued for 4 h at RT and a further Schlenk flask was prepared with 10 ml of a solution of 1.06 eq. (0.54 ml) benzoyl chloride in dry THF. Both solutions were cooled to −78° C. by means of an acetone/$N_2$ mixture and the first reaction mixture was then added dropwise to the benzoyl chloride solution over a period of 20 minutes. After addition was complete, the cooling bath was removed and the mixture was stirred for 18 h at RT with exclusion of light. The solvent was drawn off in a fine vacuum. The remaining substance mixture was taken up in 20 ml anhydrous n-pentane and then filtered under inert conditions. It was subsequently washed twice with 10 ml anhydrous n-pentane each time and the solvent was then removed from the filtrate with exclusion of light. The intensely yellow crystals obtained were then dried in a high vacuum and stored under argon in a refrigerator (4° C.) with exclusion of light. The product obtained (1.25 g, 63% of theory, melting point: 58° C.) already had very good purity without a purification step, which could be confirmed by GC-MS, HPLC and NMR spectroscopy.

GC-MS ($CH_2Cl_2$): m/z (rel.): 455 (M, 4%), 379 (6%), 351 (100%), 197 (44%), 120 (10%), 77 (10%).

$^1$H-NMR: $\delta_H$ (400 MHz, $CDCl_3$): 7.82-7.28 (20H, m, Ar—H). $^{13}$C-NMR: $\delta_C$ (100 MHz, $CDCl_3$): 161.35 (C=O);

141.56; 137.24; 136.14; 135.11; 132.64; 128.31; 128.04; 127.82; 127.73 ($C_{arom}$). $^{119}$Sn-NMR: $\delta_{Sn}$ (CDCl$_3$): −217.74.

The absorption spectrum of an acetonitrile solution of BtPhSn with a concentration of 1.0 mmol/l in comparison with benzoyltrimethylgermanium is shown in FIG. 1. The absorption maximum of BtPhSn lies at 430 nm (benzoyltrimethylgermanium: 411 nm) and the absorption coefficient is 309 l/cm·mol (benzoyltrimethylgermanium: 146 l/cm·mol). Moreover, in the case of BtPhSn it is only at wavelengths above 500 nm where significant absorption is no longer observed, whereas in the case of benzoyltrimethylgermanium this already occurs from approximately 465 nm. The comparison shows that the benzoyl chromophore of the Sn compound absorbs more strongly and at longer wavelengths compared with the Ge compound, which is advantageous for use as photoinitiator.

Example 2

Photolysis of a Solution of BtPhSn

Figure 2:
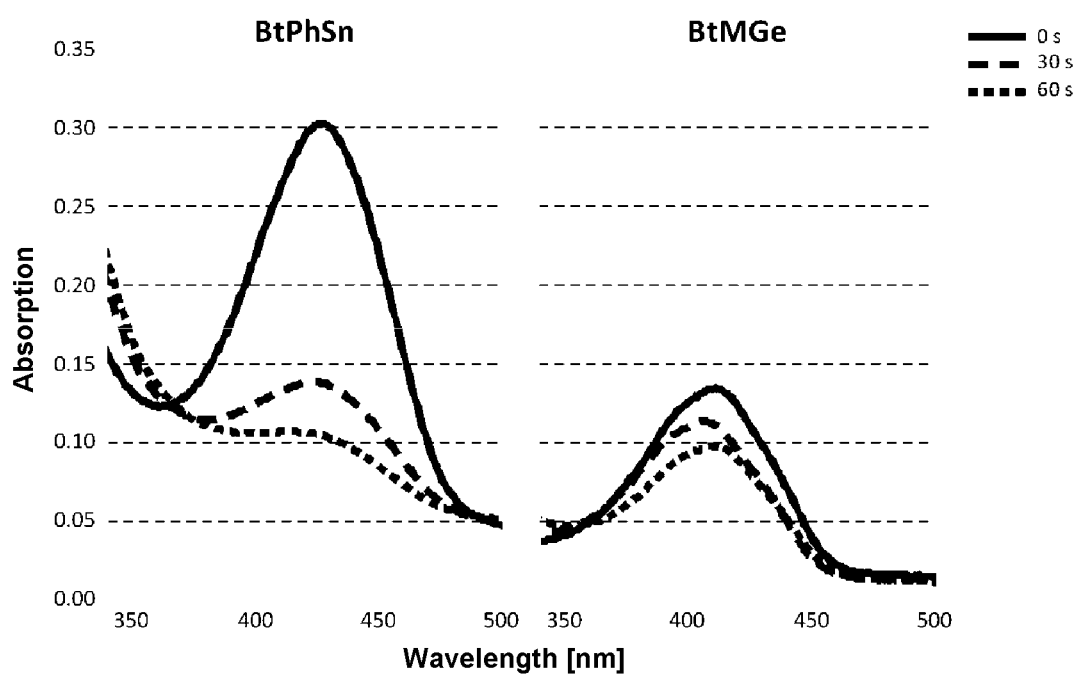
FIG. 2 shows an absorption spectrum as a function of the irradiation time of BtPhSn in comparison with BtMGe.

An acetonitrile solution of BtPhSn from Example 1 with a concentration of 1.0 mmol/l and an MMA concentration of 0.5 mol/l was irradiated in a 1 cm cuvette with the Bluephase 20 i polywave LED (Ivoclar Vivadent AG) with a broadband spectrum of 385-515 nm similar to halogen and the absorption spectrum was recorded as a function of the irradiation time. The results are represented in FIG. 2 in comparison with benzoyltrimethylgermanium (BtMGe). The results prove that, on irradiation, the Sn photoinitiator BtPhSn is clearly bleached more quickly than an analogous Ge photoinitiator BtMGe.

Example 3

Preparation of Light-Curable Composites Using Benzoyltriphenyltin (BtPhSn) from Example 1

From a mixture (figures in wt.-%) of the dimethacrylates UDMA (addition product of 2-hydroxyethyl methacrylate and 2,2,4-trimethylhexamethylene diisocyanate) and TEGDMA (triethylene glycol) and Bis-GMA (addition product of methacrylic acid and bisphenol A diglycidyl ether) and the Sn photoinitiator BtPhSn from Example 1 as well as fillers: OX-50, sil. (silanized pyrogenic silica, Degussa), YbF$_3$ (ytterbium trifluoride, Sukgyung, South Korea), SiO$_2$—ZrO$_2$ mixed oxide, sil. (silanized SiO$_2$—ZrO$_2$ mixed oxide, Transparent Materials, USA) and glass filler GM 27884, sil. (silanized glass filler GM 27884, 1.0 µm, Schott) (Table 1), the light-curing composites C1 (cement-like consistency) and C2 (filling composite) were prepared by means of an "Exakt" roller mill (Exakt Apparatebau, Norderstedt).

TABLE 1

Composition of the composites C1 and C2

| Component/resin [wt.-%] | C1 | C2 |
|---|---|---|
| BtPhSn | 0.82 | 0.10 |
| UDMA | 31.34 | 7.49 |
| TEGDMA | 7.86 | 4.05 |
| Bis-GMA | — | 8.46 |
| OX-50, sil. | 41.21 | 1.02 |
| YbF$_3$ | 18.77 | 17.21 |
| SiO$_2$—ZrO$_2$ mixed oxide, sil. | — | 10.12 |
| Glass filler GM 27884, sil. | — | 51.55 |

Corresponding test pieces were prepared from the materials, irradiated twice for 3 minutes with a dental light source (Spectramat®, Ivoclar Vivadent AG) and thereby cured. The flexural strength and the flexural modulus of elasticity were determined according to ISO standard ISO-4049 (Dentistry—Polymer-based filling, restorative and luting materials) after 24 h storage of the test pieces at room temperature (RT) or 24 h storage in water at 37° C. (WS) (Table 2).

TABLE 2

Flexural strength and flexural modulus of elasticity of the polymerized composites C1 and C2

| Parameter | C1 | C2 |
|---|---|---|
| FS[1], RT | 99.8 ± 8.0 | 66.1 ± 3.4 |
| FS[1], WS | 116.7 ± 7.6 | 72.7 ± 6.6 |
| FME[2], RT | 4.60 ± 0.18 | 3.71 ± 0.15 |
| FME[2], WS | 5.03 ± 0.20 | 3.92 ± 0.30 |

[1]Flexural strength (FS) in MPa
[2]Flexural modulus of elasticity (FME), GPa

The invention claimed is:

1. A polymerizable composition, comprising,
(a) 0.001 to 5 wt.-% of at least one acyltin compound according to the general formula (I), as photoinitiator,

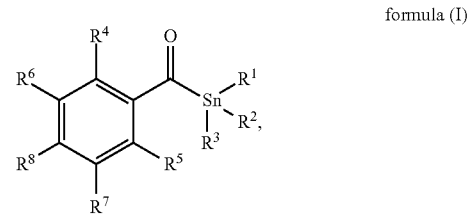

formula (I)

(b) 10 to 99.999 wt.-% radically polymerizable binder,
(c) 0 to 85 wt.-% filler and
(d) 0 to 70 wt.-% additive(s),
in each case relative to the total mass of the composition,
in which the variables of formula (I) have the following meanings:
R$^1$, R$^2$, R$^3$ independently of each other are in each case a group of the formula (II)

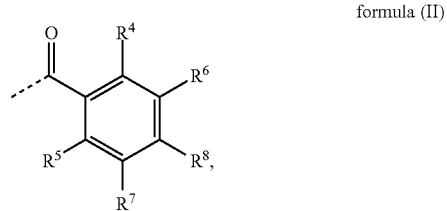

formula (II)

an aromatic C$_{6-30}$ radical, which can be substituted by one or more cyclic, branched or linear C$_{1-20}$-alkyl, C$_{1-20}$-alkenyl, C$_{1-20}$-alkoxy, C$_{1-20}$-alkylthio or C$_{1-20}$-alkenoxy radicals, wherein the named substituents themselves can be interrupted one or more times by —O—, —S— or —NR$^9$- and/or can be substituted by one or more radically polymerizable groups and/or radicals R$^{10}$,
a cyclic, branched or linear C$_{1-20}$-alkyl, C$_{1-20}$-alkenyl, C$_{1-20}$-alkoxy, C$_{1-20}$-alkylthio, C$_{1-20}$-alkenoxy or C$_{1-20}$-acyloxy radical, which can be interrupted one or more times by —O—, —S— or —NR$^9$- and/or can be substituted by one or more radically polymerizable groups and/or radicals R$^{10}$, or a benzoyloxy radical, —H, trimethylsilyl, —OH, halogen or —CN, wherein R$^1$ and R$^2$, taken together, can also represent a double-bonded oxygen or sulfur atom or, together with the Sn atom to which they are bonded, can form an aliphatic saturated or unsaturated ring which in addition to the Sn atom contains 2 to 6 carbon atoms and optionally one or more oxygen atoms, wherein one or more carbon atoms can be substituted by a double-bonded oxygen atom and/or the ring can be fused with an aromatic ring, R$^4$, R$^5$, R$^6$, R$^7$, R$^8$ independently of each other are in each case —H, a cyclic, branched or linear C$_{1-20}$-alkyl, C$_{1-20}$-alkenyl, C$_{1-20}$-alkyloxy or C$_{1-20}$-alkenoxy radical, which can be interrupted one or more times by —O—, —S— or —NR$^9$- and/or can be substituted by one or more radically polymerizable groups and/or radicals R$^{10}$, or —OR$^9$, halogen, —SR$^9$, —N(R$^9$)$_2$, —CF$_3$, —CN, —NO$_2$, —COOR$^9$ or —CONHR$^9$, R$^9$ is —H or a cyclic, branched or linear C$_{1-20}$-alkyl or C$_{1-20}$-alkenyl radical and R$^{10}$ is —OH, —C$_x$F$_{2x+1}$ with x=1 to 20 or —[Si(CH$_3$)$_2$]$_y$—CH$_3$ with y=1 to 20.

2. The polymerizable composition according to claim 1, in which, in each case independently of each other, R$^1$, R$^2$, R$^3$ independently of each other are in each case a group of the formula (II), an aromatic C$_{6-15}$ radical, which can be substituted by one or more branched or linear C$_{1-12}$-alkyl or C$_{1-12}$-alkoxy radicals, wherein the named substituents themselves can be interrupted one or more times by —O— and/or can be substituted by one or more radically polymerizable groups and/or —OH, or a branched or linear C$_{1-12}$-alkyl, C$_{1-12}$-alkenyl, C$_{1-12}$-alkoxy, C$_{1-12}$-alkylthio or C$_{1-12}$-acyloxy radical, which can be interrupted one or more times by —O— and/or can be substituted by one or more radically polymerizable groups and/or —OH, or a benzoyloxy radical, trimethylsilyl, —OH, halogen or —CN, wherein R$^1$ and R$^2$, taken together, can also represent a double-bonded oxygen or sulfur atom or, together with the Sn atom to which they are bonded, can form an aliphatic saturated or unsaturated ring which in addition to the Sn atom contains 2 to 6 carbon atoms and optionally one or more oxygen atoms, wherein one or more carbon atoms can be substituted by a double-bonded oxygen atom and/or the ring can be fused with an aromatic six-membered, ring, R$^4$, R$^5$, R$^8$ independently of each other are in each case —H, a branched or linear C$_{1-12}$-alkyl, C$_{1-12}$-alkenyl, C$_{1-12}$-alkyloxy or C$_{1-12}$-alkenoxy radical, which can be interrupted one or more times by —O— and/or can be substituted by one or more radically polymerizable groups and/or —OH, or —OR$^9$, halogen, —SR$^9$, —N(R$^9$)$_2$, —CF$_3$, —CN or —NO$_2$, R$^6$, R$^7$ independently of each other are in each case —H or —F or a branched or linear C$_{1-12}$-alkyl, C$_{1-12}$-alkenyl, C$_{1-12}$-alkyloxy or C$_{1-12}$-alkenoxy radical, which can be interrupted one or more times by —O— and/or can be substituted by one or more radically polymerizable groups and/or —OH, and R$^9$ is —H or methyl.

3. The polymerizable composition according to claim 1, in which, in each case independently of each other, R$^1$, R$^2$, R$^3$ independently of each other are in each case a group of the formula (II), phenyl, trimethylphenyl, a branched or linear C$_{1-8}$-alkyl, C$_{1-12}$-alkylthio or C$_{1-12}$-acyloxy radical, a benzoyloxy, vinyl or methacryloyl radical, trimethylsilyl, —OH, —Cl or —CN, wherein R$^1$ and R$^2$, taken together, can also represent a double-bonded oxygen or sulfur atom or, together with the Sn atom to which they are bonded, can form a dioxastannepin ring, wherein one or two carbon atoms of the dioxastannepin ring can be substituted by a double-bonded oxygen atom and/or the ring can be fused with a benzene ring, R$^4$, R$^5$, R$^8$ independently of each other are in each case —H, a branched or linear C$_{1-8}$-alkyl radical, which can be interrupted by 1 to 3 O atoms and/or can be substituted by vinyl, or —OR$^9$, halogen, —SR$^9$, —N(R$^9$)$_2$, —CF$_3$, —CN or —NO$_2$, R$^6$, R$^7$ independently of each other are in each case —H, —F or a branched or linear C$_{1-8}$-alkyl radical, which can be interrupted by 1 to 3 O atoms and/or can be substituted by vinyl, and R$^9$ is —H or methyl.

4. The polymerizable composition according to claim 1, in which, in each case independently of each other, R$^1$, R$^2$, R$^3$ independently of each other are in each case a group of the formula (II), phenyl, a linear C$_1$-C$_8$-alkyl radical or trimethylsilyl, R$^4$, R$^5$, R$^8$ independently of each other are in each case —H, methyl, —OR$^9$ or —F, R$^6$, R$^7$ independently of each other are in each case —H or —F and R$^9$ is —H or methyl.

5. The polymerizable composition according to claim 1, comprising at least one radically polymerizable monomer and/or prepolymer as the at least one polymerizable binder.

6. The polymerizable composition according to claim 5, comprising at least one mono- or multifunctional (meth)acrylate or a mixture thereof as the at least one polymerizable binder.

7. The polymerizable composition according to claim 1 for use as dental material.

8. The polymerizable composition according to claim 7 for intraoral use as cement, filling composite or veneering material.

9. The polymerizable composition according to claim 1 for use as dental cement, comprising
(a) 0.001 to 5 wt.-% acyltin compound(s) of the general formula (I),
(b) 10 to 50 wt.-% radically polymerizable binder,
(c) 40 to 70 wt.-% filler and
(d) 0 to 5 wt.-% additive(s).

10. The polymerizable composition according to claim 1 for use as dental composite, comprising
(a) 0.001 to 5 wt.-% acyltin compound(s) of the general formula (I),
(b) 10 to 40 wt.-% radically polymerizable binder,
(c) 50 to 85 wt.-% filler and
(d) 0 to 5 wt.-% additive(s).

11. The polymerizable composition according to claim 1 for use as dental coating material, comprising
(a) 0.001 to 5 wt.-% acyltin compound(s) of the general formula (I),
(b) 10 to 99.989 wt.-% radically polymerizable binder,
(c) 0 to 20 wt.-% nanoparticulate filler,
(d) 0.01 to 2 wt.-% additive(s) and
(e) 0 to 70 wt.-% solvent.

12. The polymerizable composition according to claim 1 for use as dental adhesive, comprising
   (a) 0.001 to 5 wt.-% acyltin compound(s) of the general formula (I),
   (b) 10 to 99.989 wt.-% radically polymerizable binder,
   (c) 0 to 20 wt.-% nanoparticulate filler and
   (d) 0.01 to 2 wt.-% additive,
   (e) 0 to 50 wt.-% solvent and
   (f) 1 to 20 wt.-% radically polymerizable adhesive monomer.

13. The polymerizable composition according to claim 1 for use as material for stereolithography or 3D printing, comprising
   (a) 0.001 to 5 wt.-% acyltin compound(s) of the general formula (I),
   (b) 10 to 99 wt.-% radically polymerizable binder,
   (c) 0 to 80 wt.-% filler(s) and
   (d) 0 to 10 wt.-% additive(s).

14. The polymerizable composition according to claim 1 for use as coating material, comprising
   (a) 0.001 to 5 wt.-% acyltin compound(s) of the general formula (I),
   (b) 20 to 99 wt.-% radically polymerizable binder,
   (c) 0 to 20 wt.-% dye(s) and/or pigment(s) and
   (d) 0 to 10 wt.-% further additive(s).

15. The polymerizable composition according to claim 1 for use as printing ink, comprising
   (a) 0.001 to 5 wt.-% acyltin compound(s) of the general formula (I),
   (b) 20 to 95 wt.-% radically polymerizable binder,
   (c) 1 to 20 wt.-% dye(s) and/or pigment(s) and
   (d) 0 to 10 wt.-% further additive(s).

16. The polymerizable composition according to claim 2, wherein $R^1$ and $R^2$, taken together, can also represent a double-bonded oxygen or sulfur atom or, together with the Sn atom to which they are bonded, can form an aliphatic saturated or unsaturated ring which in addition to the Sn atom contains 4 carbon atoms and 2 oxygen atoms, wherein 2 carbon atoms can be substituted by a double-bonded oxygen atom and/or the ring can be fused with an aromatic, six-membered, ring.

* * * * *